United States Patent [19]

Gaynor et al.

[11] Patent Number: 5,688,511
[45] Date of Patent: Nov. 18, 1997

[54] CELLULAR PROTEIN TDP-43 AND REGULATION OF HIV-1 GENE EXPRESSION

[75] Inventors: Richard B. Gaynor; S.-H. Iqnatius Ou, both of Dallas; Foon Kin Wu, Carrollton, all of Tex.

[73] Assignee: Board of Regents, The University of Texas System, Austin, Tex.

[21] Appl. No.: 343,682

[22] Filed: Nov. 22, 1994

Related U.S. Application Data

[63] Continuation-in-part of Ser. No. 788,266, Nov. 5, 1991, Pat. No. 5,350,835, and Ser. No. 239,047, May 6, 1994, abandoned.

[51] Int. Cl.[6] ................................................. C12N 5/06
[52] U.S. Cl. .................... 424/207.1; 530/358; 530/350; 930/220; 536/23.72; 424/278.1; 514/12; 435/375
[58] Field of Search .................... 435/5, 974, 240.2; 530/350, 358; 930/220; 536/23.72; 424/207.1, 278.1

[56] References Cited

PUBLICATIONS

Dialog Search Report (1991).
Garcia et al. (1989), The EMBO Journal, 8(3): 765–778, Human immunodeficiency virus type 1 Ltr TATA and TAR region sequences required for transcriptional regulation.
Marciniak et al. (1990), Cell, 63: 791–802, HIV–1 TAT Protein Trans–Activates Transcription In Vitro.
Berkhout et al. (1989), Cell, 59: 273–282, TAT Trans–Activates the Human Immunodeficiency Virus Through a Nascent RNA Target.
Laspia et al. (1990), Genes & Development, 4:2397–2408, Synergy between HIV–1 TAT and adenovirus E1A is principally due to stabilization of transcriptional elongation.
Marciniak et al. (1990), Proc. Natl. Acad. Sci. USA, 87:3624–3628, Identification and characterization of a HeLa nuclear protein that specifically binds to the trans–activation–response (TAR) element of human immunodeficiency virus.
Garcia et al. (1987), The EMBO Journal, 6(12):3761–3770, Interactions of cellular proteins involved in the transcriptional regulation of the human immunodeficiency virus.
Gaynor et al. (1989), Proc. Natl. Acad. Sci. USA, 86:4858–4862, Specific binding of a HeLa cell nuclear protein to RNA sequences in the human immunodeficiency virus transactivating region.
Harrich et al. (1990), The EMBO Journal, 9(13):4417–4423, TAR independent activation of the human immunodeficiency virus in phorbol ester stimulated T lymphocytes.
Roy et al. (1990), Genes & Development, 4:1365–1373, A bulge structure in HIV–1 TAR RNA is required for Tat binding and Tat mediated trans–activation.
Pearson et al. (1990), Proc. Natl. Acad. Sci. USA, 87:5079–5083, A transdominant tat mutant that inhibits tat–induced gene expression from the human immunodeficiency virus long terminal repeat.
Wu et al. (1988), The EMBO Journal, 7(7):2117–2129, :Purification of the human immunodeficiency virus type 1 enhancer and TAR binding proteins EBP–1 and UBP–1.
Dignam et al. (1983), Nucleic Acids Research, 11(5):1475–1488, Accurate transcription initiation by RNA polymerase II in a soluble extract from isolated mammalian nuclei.
Field et al. (1988), Molecular and Cellular Biology, 8(5):2159–2165, Purification of a RAS–Responsive Adenylyl Cyclase Complex from Saccharomyces cerevisiae by Use of an Epitope Addition Method.
Gatignol et al. (1989), Proc. Natl. Acad. Sci. USA, 86:7828–7832, Identification of cellular proteins that bind to the human immunodeficiency virus type 1 trans–activation–responsive TAR element RNA.
Goody et al. (1991), FEBS Letters (pp. 1–5), Factors contributing to the inhibition of HIV reverse transcriptase by chain–terminating nucleotides in vitro and in vivo.
Calnan et al. (1991), Genes & Development, 5:201–210, Analysis of arginine–rich peptides from the HIV Tat protein reveals unusual features of NRA–protein recognition.
Wu et al. (1991), Genes & Development, 5(11):2128–2140, tat regulates binding of the human immunodeficiency virus trans–activating region RNA loop–binding protein TRP–185.
Gaynor (1991), Role of the TAR Element in Regulating HIV Gene Expression, In: Advances in Molecular Biology and Targeted Treatment of AIDS, pp. 79–90.
Gaynor, R. (1991), Cellular Factors Involved in Regulating HIV Gene Expression, In: Genetic Structure and Regulation of HIV, Haseltine and Wong–Staal, editors: pp.107–134.
Waterman et al. (1991), Nuclear Proteins Implicated in HIV–1 Transcriptional Control, In: Genetic Structure and Regulation of HIV, Haseltine and Wong–Staal, editors: pp. 391–403.

(List continued on next page.)

*Primary Examiner*—Christine M. Nucker
*Assistant Examiner*—Jeffrey Stucker
*Attorney, Agent, or Firm*—Arnold, White & Durkee

[57] ABSTRACT

Compositions including a polypeptide or nucleic acid sequence encoding a polypeptide that binds TAR DNA (particularly the region –18 to +28 of HIV-LTR DNA) and that does not bind to TAR RNA (particularly the region +1 to +80 of the TAR RNA) are disclosed. The cellular binding protein TDP-43 including the polypeptide has an estimated molecular weight of between about 40 kD and 46 kD as determined by SDS polyacrylamide gel electrophoresis. Fusion proteins that include the entire cellular binding protein TDP-43 or fragments thereof are also described. The cellular binding protein, peptide fragments and nucleic acid sequences encoding them, repress HIV gene expression. Methods for preparing the cellular binding protein from cells as recombinant proteins with recombinant host cells are also disclosed. Antibodies to the TDP-43 cellular binding protein are also described. The isolated nucleic acid sequences of the protein and its fragments are described in the construction of retroviral vectors. Methods for using the cellular binding protein, polypeptides thereof, and nucleic acid sequences encoding the protein and its fragments in the preparation of pharmaceutical preparations and in methods for repressing HIV gene expression are also disclosed.

20 Claims, 2 Drawing Sheets

PUBLICATIONS

Marciniak et al. (1990), Proceedings of the National Academy of Science, USA, 87:3624–3628, Identification and Characterization of a HeLa Nuclear Protein that Specifically Binds to the Transactivation Response (TAR) Element of Human Immuno Deficiency Virus.

Gatignol et al. (1989), Proceedings of the National Academy of Science, USA, 86:7828–7832, Identification of Cellular proteins that Bind to the Human Immunodeficiency Virus Type I Trans-Activation-Response TAR Element RNA.

Gaynor et al. (1989), Proceedings of the National Academy of Science, USA, 86:4858–4862, Specific Binding of a HeLa Cell Nuclear Protein to RNA Sequences in the Human Immunodeficiency Virus Trans-Activating Region.

Wu et al. (1988), The EMBO Journal, 7(7):2117–2129, Purification of the Human Immunodeficiency Virus Type I Enhancer and TAR Binding Proteins EBP-1 and UBP-1.

Garcia et al. (1989), The EMBO Journal, 8(3):765–778, Human Immunodeficiency Virus Type I LTR TATA and TAR Region Sequences Required for Transcriptional Regulation.

Wu et al. (1991), Genes and Development, 5(11):1935–2152, tat Regulated Binding of the Human Immunodeficiency Virus Trans-Activating Region RNA Loop-Binding Protein TRP-185.

Sheline et al. (1991), Genes and Development, 5(12b):2508–2520, Two distinct nuclear transcription factors recognize loop and bulge residues of the HIV-1 TAR RNA hairpin.

Gaynor, R. (1992), AIDS, 6(4):347–363, Cellular transcription factors involved in the regulation of HIV-1 gene expression.

International Search Report, No. 92/09546 (Feb. 1993).

Calvert et al., "Cloning and characterization of a novel sequence-specific DNA-binding protein recognizing the negative regulatory element (NRE) region of the HIV-1 long terminal repeat," Gene, 101:171–176, 1991.

Du et al., "Human transcription factor USF stimulates transcription through the initiator elements of the HIV-1 and the Ad-ML promoters," The EMBO Journal, 12(2):501–511, 1993.

Morgenstern and Land, "Advanced mammalian gene transfer: high titre retroviral vectors with multiple drug selection markers and a complementary helper-free packaging cell line," Nucleic Acids Research, 18(12):3587–3596, 1990.

Olsen et al., "Interaction of Cellular Factors with Intragenic Cis-Acting Repressive Sequences within the HIV Genome," Virology, 191:709–715, 1992.

Reddy, "Regulation of HIV-1 Gene Expression by Cellular Transcription Factors," Pathobiology, 60:219–224, 1992.

West et al., "Characterization and Purification of a Novel Transcriptional Repressor from HeLa Cell Nuclear Extracts Recognizing the Negative Regulatory Element Region of Human Immunodeficiency Virus-1 Long Terminal Repeat," The Journal of Biological Chemistry, 267(35):24948–24952, 1992.

CELLULAR PROTEIN TDP-43 AND REGULATION OF HIV-1 GENE EXPRESSION

The present application is a continuation-in-part of U.S. Ser. No. 07/788,266, now U.S. Pat. No. 5,350,835, filed Nov. 5, 1991 and U.S. Ser. No. 08/239,047, filed May 6, 1994 now abandoned.

The government owns certain rights in the present invention pursuant to grant number AI25288 from the National Institute of Health and grant 001 from the Veterans Administration.

1. FIELD OF THE INVENTION

The present invention relates to the field of cellular proteins, most particularly, cellular proteins capable of binding DNA and regulating gene expression. The present invention also relates to the field of cloning and characterizing cellular proteins that bind viral DNA. The invention also relates to the field of therapeutic methods and reagents for the treatment of vital diseases, such as AIDS and HIV-related pathologies.

2. BACKGROUND OF THE RELATED ART

Gene expression of the human immunodeficiency virus (HIV) is regulated by a variety of mechanisms. The long terminal repeat (LTR) is the site of multiple regulatory regions involved in both general and tissue specific gene expression.

HIV is recognized as the causative agent of Acquired Immunodeficiency Syndrome (AIDS). Therapeutic agents which have been used in the treatment of AIDS include AZT (azidothymidine) and DDI (dideoxyinosine) (Marciniak, R. A. et al., 1990). Both of these agents are nucleotide analogs that target the viral enzyme, reverse transcriptase. While these agents have been used with varying degrees of success, they are also unfortunately associated with a variety of severe side effects. Some of these side effects include peripheral neuropathy (DDI), pancreatitis, granulocytopenia, anemia, severe headache, nausea, insomnia, neurotoxicity, and seizure. These agents have also been associated with a potential carcinogenicity and teratogenicity (Marciniak, R. A. et al., 1990).

Other molecular targets under investigation as anti-viral targets include an HIV-gene encoded protease. The protease is encoded on the polygene of HIV-1. The polygene encodes three proteins—a reverse transcriptase, a self-cleaving protease (that is required for processing the reverse transcriptase) and a nuclease that is essential for integration of vital DNA into the genome of a host cell. Inhibitors of the HIV protease have been developed using the crystal structure of the protein.

Other potential molecular targets for affecting vital gene expression include the glycosylated envelope protein of HIV and the receptor protein CD4. CD4 is a T cell co-receptor glycoprotein on the surface of lymphocytes to which the virus binds. A soluble form of CD4 can bind to the vital envelope protein and prevent the virus from entering cells. Alternatively, a conjugate of CD4 and a toxin might be used to attack HIV-infected cells, since such cells express the envelope protein on their surfaces. Another drug, dextran sulfate, has also been used in the treatment of AIDS. This drug blocks the binding of HIV to target cells.

None of these molecular targets for anti-viral therapy relates to an agent of cellular origin capable of specifically affecting vital gene expression. An enhanced understanding of the particular role of cellular proteins in the molecular events of both cellular and viral (HIV) gene expression would provide a new avenue for the development of effective anti-viral agents. Such information would further provide for the development of a new genus of drugs based on the regulation of host proteins for the treatment of AIDS and AIDS-related diseases.

Multiple regulatory elements in the HIV-1 LTR are critical in controlling the level of gene expression (Gaynor, 1992). These elements, such as, NF-κB (Nabel and Baltimore, 1987), Sp1 (Jones et al., 1988), TATA (Berkhout et al., 1990; Garcia, 1987; Jones et al., 1988; Lu et al., 1993; Olsen and Rose, 1992), and TAR (Garcia, 1987; Jones et al., 1986; Kato et al., 1992; Sheline et al., 1991; Wu, 1991; Wu et al., 1988) serve as binding sites for a variety of cellular transcription factors that may either directly or indirectly influence the degree of transactivation by a protein called Tat. The exact mechanism by which Tat stimulates gene expression is not known, though effects on both transcriptional initiation and elongation seem likely (Finberg et al., 1991; Kao, 1987; Kato et al., 1992; Laspia et al., 1989; Marciniak and Sharp, 1991; Ratnasabapathy et al., 1990). Identifying cellular transcription factors that modulate Tat function is, therefore, critical in understanding the mechanisms regulating HIV-1 gene expression.

One regulatory element in the HIV-1 LTR known as TAR is critical for Tat-activation (Rosen et al., 1985). The TAR element, which extends from −18 to +80 in the HIV-1 LTR, is transcribed into a stable stem loop RNA structure between +1 and +60 that is critical for Tat activation (Berkhout and Jeang, 1992; Feng and Holland, 1988; Garcia et al., 1989; Hauber and Cullen, 1988; Selby and Peterlin, 1990). At least three regions within TAR RNA including the stem structure, the bulge, and the loop sequences are each required for high level of Tat activation (Berkhout et al., 1989; Feng and Holland, 1988; Garcia et al., 1989; Roy et al., 1990). The bulge region in TAR RNA serves as the binding site for Tat (Calnan et al., 1991; Dingwall et al., 1990; Weeks and Crothers, 1991), while the loop sequences serve as the binding site for the cellular factor TRP-185 (Sheline et al., 1991; Wu et al., 1991). The use of heterologous promoter constructs has demonstrated that the presence of TAR is sufficient to confer responsiveness to Tat (Berkhout et al., 1990; Ratnasabapathy et al., 1990). In addition, recent studies indicate that HIV-1 viruses containing TAR element mutations exhibit markedly decreased growth properties (Harrich et al., 1990).

In contrast to the established role of TAR RNA on modulating HIV-1 gene expression, the function of TAR DNA remains less clear. DNase I footprinting, utilizing both HeLa and T-lymphocyte nuclear extracts, reportedly gave extensive protection over TAR DNA extending from −10 to +52 (Garcia et al., 1989; Garcia et al., 1987; Jones et al., 1986; Malim et al., 1989). Chromatographic fractionation of HeLa nuclear extract was reported to result in the purification of a 64 kDa protein designated UBP-1 or LBP-1 (Wu et al., 1988) that binds to multiple sites present in both TAR DNA and sequence motifs flanking the TATA box (Jones et al., 1986; Kato et al., 1992; Wu et al., 1988). The binding of purified UBP-1/LBP (Kato et al., 1992) to these latter sites reportedly represses HIV-1 gene expression in in vitro transcription assays. UBP-1 or LBP-1 reportedly is a 64/62 kDa protein, and in addition to binding to TAR DNA between nucleotides +2 and +6, UBP-1/LBP-1 also binds to a lower affinity site adjacent to the HIV-1 TATA element and prevents the binding of the TFIID complex to the TATA box (Kato et al., 1992). However, the role of these proteins on modulating the level of Tat-activation has not been elucidated. Other proteins, such as CTF/NF1, have also been reported to bind to downstream regions of TAR DNA, though their roles in HIV-1 gene regulation remain to be determined (Jones, 1986).

Another TAR DNA element has also been implicated in the generation of short, non-processive transcripts that terminate at the base of the TAR RNA stem loop structure in the absence of Tat, and are transcribed from the HIV-1 promoter (Ratnasabapathy et al., 1990; Sheldon et al., 1993). The regulatory element responsible for the generation of these transcripts, designated the inducer of short transcripts (IST), has been reportedly mapped to a DNA element in TAR located between nucleotides −4 and +25 (Sheldon et al., 1993). When TAR is placed downstream of a variety of heterologous promoters, IST possesses enhancer activity that generates high levels of short transcripts that terminate approximately at nucleotide +60 (Ratnasabapathy et al., 1990). Though the generation of these short transcripts is not required for Tat activation, such transcripts may play an important role in other facets of the HIV-1 life cycle, such as viral latency.

Not only is there no currently known cure for AIDS and AIDS related diseases, there is currently no effective treatment for long-term suppression of HIV-1 infection. The TAR region of the HIV DNA may possess distinct regulatory elements that play an important role in modulating HIV-1 gene expression. Given the importance of TAR in the regulation of HIV-1 gene expression, it is important to identify and characterize additional cellular proteins that bind to the TAR DNA region and determine their potential roles on HIV-1 gene expression in order to provide further treatment protocols. The medical arts is also in need of well characterized molecular tools, such as cellular proteins, for creating medicinal agents targeted at inhibiting HIV.

It is an object of the invention to provide a tool which is useful in the characterization of viral and cellular gene expression. It is still another object of the invention to provide a reagent which is useful in the study of viral gene regulation.

It is still a further object of this invention to provide a better, more reliable and convenient procedure for monitoring the expression of TDP-43 protein. Another object is to allow for the monitoring of the progression of HIV disease. For example, levels of the TDP-43 cellular binding protein would be monitored with the herein described anti-TDP-43 antibody. Decreases in the level of the TDP-43 protein in a patient sample would be identified and used as a parameter for monitoring the progression of the disease. A decrease in the amount of TDP-43 protein in a patient sample over time would be used to identify a progression of the disease, together with other, clinically observable symptoms of AIDS and HIV infection well known to those of ordinary skill in the medical arts.

It is another object of the invention to provide a method for monitoring HIV-disease progression and to provide a method for treating HIV-disease. How these and other objects of the invention are achieved will become apparent in light of the accompanying disclosure.

SUMMARY OF THE INVENTION

The present invention addresses one or more of the problems in the art relating to the characterization and control of gene expression, particularly vital HIV gene expression.

The present invention also addresses the need for highly specific alternative AIDS and AIDS-related disease therapeutic agents. The agents, nucleic acid sequences, proteins, polypeptides and compositions including them, target particular molecular events of HIV gene expression by controlling activity of a polypeptide that binds to a TAR region of HIV-1 LTR DNA, does not bind to TAR RNA, and that represses (inhibits) HIV-1 gene expression. This polypeptide is designated herein as a "TDP-43" protein. As used in the description of the present invention, the term TDP-43 is intended to include a cellular binding protein or a polypeptide fragment of a cellular binding protein, or dimeric or other forms of the protein, that binds any portion of a TAR region of an HIV-1 LTR DNA, or specifically to a region −18 to +28 of the HIV LTR-DNA, that does not bind TAR RNA, or specifically does not bind a region +1 to −80 of the TAR RNA, and that represses or inhibits HIV-1 gene expression. In particular embodiments, the polypeptide is further defined as including a sequence 7–125 of SEQ ID NO: 1.

The polypeptides of the invention are cellular polypeptides that bind HIV nucleic acid other than HIV RNA, and in so doing inhibit transcription from the long terminal repeat of HIV. These polypeptides therefore provide a method for inhibiting HIV gene expression. Thus, a tool for inhibiting the expression of viruses such as HIV and HTLV is disclosed.

An RNP binding motif further characterizes particular embodiments of the TRP-43 cellular binding polypeptides of the present invention. In some embodiments, the protein or polypeptide fragment comprises both an RNP-1 and an RNP-2 region of an RNP binding motif. However, the protein or polypeptide fragment will bind HIV-1 LTR DNA where only a portion of the motif, such as a portion corresponding to the RNP-1 region, is included in the sequence of the polypeptide.

In particular embodiments, the polypeptide may be further described as being encoded by a sequence of about 118 to about 1,000 amino acids in length, and in other embodiments, as being encoded by a sequence of about 115 to about 450 amino acids in length. By way of example, such amino acid sequences encoding the polypeptide are sequences corresponding to 92–125, 7–125, 7–166, 7–198, 7–240, 7–333, 7–414, 7–421 or 92–315 of the amino acid sequence provided at SEQ ID NO: 1. The polypeptides may be further defined as being encoded by particular nucleic acid sequences 276–375, 21–375, 21–498, 21–594, 21–720, 21–999 or 21–1242, 21–1263 or 276–375 of SEQ ID NO: 2.

The polypeptides and the full length protein may also take the form of fusion proteins. In particular embodiments, the polypeptide has been expressed as a fusion protein with glutathione S-transferase. In still other embodiments, the polypeptide may take the form of a fusion protein comprising the TDP-43 protein or polypeptide fragment and a gene 10 protein. However, many other second proteins may be used in preparing these fusion proteins, as well as a third, fourth, fifth, sixth or more additional protein or polypeptide sequences in constructing fusion proteins of the present invention.

The invention provides for the preparation and use of these polypeptides and proteins, as singular proteins or peptides, or as fusion proteins. These preparations may be further used as target antigen for the detection of anti-TDP-43 antibody in a biological sample. These preparations and compositions including these compositions are useful in themselves, as well as in the development of diagnostic methods and pharmaceutical preparations. By way of example, these preparations are expected to be useful in the treatment of HIV infection.

The amino acid sequence and messenger RNA that encode the cellular binding protein TDP-43, and polypeptide fragments of TDP-43, have been isolated and characterized. Knowledge of the sequences that encode the TDP-43 protein and polypeptide fragments thereof is useful in the preparation of expression vectors, molecular probes, and retroviral vectors. The expression vectors are used to transform whole cells, the cells then producing recombinant forms of the TDP-45 cellular protein, as well as polypeptide fragments and antigenic and/or therapeutic polypeptides of the protein. Preparations of the recombinent protein or polypeptides in a sterile solution may also be provided for therapeutic use. It is further proposed that the polypeptides and proteins prepared containing these polypeptides will be useful in the preparation of immunodiagnostic agents and therapeutic agents (and more specifically, inhibitors) for the treatment of HIV-related diseases (i.e. AIDS, ARC, or AIDS related pathologies (e.g., Karposi's sarcoma and lymphoma)).

The polypeptides of the present invention may be further described as comprising a DNA binding element. This DNA binding element in some embodiments comprises a cellular protein TDP-43 or polypeptide fragment thereof capable of binding with specificity and high affinity to a TAR region of DNA, and that does not bind TAR RNA. Even more particularly, the inventors demonstrate that the disclosed cellular binding protein and fragments thereof will bind to a −18 to +28 TAR region of the HIV LTR DNA. The presently disclosed cellular binding protein TDP-43 and polypeptides thereof are further defined as not binding TAR RNA, particularly to not bind the region +1 to +80 of TAR RNA. The DNA binding element of TDP-43 protein or a polypeptide fragment thereof is also characterized as effectively inhibiting HIV-1 gene expression.

For purposes of describing the present invention, the cellular binding protein in particular embodiments is designated "TDP-43". This particular designation was derived from the characterization of the full length purified and isolated TDP-43 cellular protein having a molecular weight of between about 40 to about 46 kD, as determined by SDS polyacrylamide gel electrophoresis, that was first isolated from mammalian cell extracts by the present inventors. Even more specifically, the molecular weight of the full length form of the isolated TDP-43 cellular protein obtained from cellular extracts was determined to have a molecular weight of about 43 kD (autoradiogram—see FIG. 4A).

The TDP-43 binding protein identified in these analysis has been determined to be in a monomer form; however, a species of 86 kDa also was found to bind DNA. This 86 kDa form is likely a dimer. Binding of the TDP-43 protein to the TAR region of HIV LTR effectively represses (inhibits) HIV gene expression from the trans-activating region of the viral DNA.

The described polypeptides of the invention may be useful alone as a tool for elucidating mechanisms of HIV and cellular gene expression. As used in the description of the present invention, the term "TAR region" is defined as a transactivating region of an HIV DNA sequence, most specifically a TAR region of the HIV LTR DNA. The TAR region to which the DNA binding element (i.e. TDP-43 cellular binding protein or polypeptide fragment thereof) binds consists of nucleotides extending from −18 to +28 of the HIV LTR DNA. Defined in terms of the particular base pairs of the TAR DNA bound, the polypeptide may be described as binding two sets of pyrimidine-rich sequences in the HIV-1 LTR between −15 and −5 and +4 and +11 (Table 2). The nucleic acid sequences of the TDP-43 defined in the segments of SEQ ID NO:2 that bind these regions in the HIV-1 LTR also constitute particular embodiments of the present invention.

The present invention also provides a highly efficient method for isolating and preparing compositions comprising the TDP-43 protein and polypeptides thereof found to bind the region of TAR DNA described herein. In one embodiment, a composition comprising the polypeptides of the present invention may be prepared by a process comprising the steps of preparing an extract of mammalian cells, and obtaining fractions of the mammalian cell extract that contain a polypeptide that binds HIV LTR DNA, that does not bind TAR RNA, and that inhibits HIV-1 gene expression. In other embodiments, the process may further comprise isolating protein or polypeptides having a molecular weight of between about 40 kD and about 46 kD as determined by SDS polyacrylamide gel electrophoresis from the fractions, or more particularly, having a molecular weight of about 43 kD. The polypeptide or protein may be further described as binding a sequence −18 to +28 of HIV LTR DNA, as not binding a sequence +1 to +80 of TAR RNA, and as inhibiting HIV gene expression.

In other embodiments, the method may further comprise selecting fractions of the mammalian cell extract eluted from a phosphocellulose column with about 0.1M to about 0.3M KCL. As will be appreciated by those of ordinary skill in the art, other buffers having the same or similar elution characteristics as obtained by the present inventors with KCL may be used with equal efficacy in the described process for preparing a composition of the polypeptide or protein having the described combination of defined characteristics. By way of example, such alternative buffers include 0.1M to 0.3M NaCl.

In another aspect of the described process, the particular mammalian cells from which the polypeptide and protein may be isolated may be further defined as human cells, such as HeLa cells. However, other types of mammalian human cells may be used in the practice of the aforedescribed processes. Most preferably, the mammalian cells are first processed to form a nuclear extract. The nuclear extract is then fractionated, with those fractions having the aforedescribed binding specificity for HIV DNA and that do not bind HIV RNA, being pooled and further purified to obtain TDP-43 binding protein or polypeptides thereof.

Mammalian cells from which the described TDP-43 may be extracted include cells that are susceptible to HIV infection or related viruses. By way of example, useful mammalian cell lines include VERO (ATCC CCL 81), HeLa cells (ATCC CCL 2.1, ATCC CCL 2.2), W138, COS, Jurkat, CEM, 293 (human embryonic kidney cell line ATCC CRL 1573) and MDCK cell lines.

The term "TAR DNA binding activity" as used in the description of the present invention relates to the ability or the demonstration of the ability of a particular composition, elements within a composition, or column fraction to bind the TAR region of HIV DNA, and is even more specifically described as a fraction having a polypeptide or protein demonstrating specific binding affinity for the TAR region of the HIV LTR DNA at a DNA region from nucleotides −18 to +28.

Nucleic Acids

The present invention also provides isolated polynucleotides and fragments thereof that encode a polypeptide or TDP-43 binding protein that binds with high specificity to a sequence −18 to +28 of HIV LTR DNA. These particular isolated polynucleotides are characterized in that they encode cellular binding proteins or fragments thereof that do not bind TAR RNA, particularly that do not bind sequences of +1 to +80 of the TAR RNA. The cellular binding proteins and fragments thereof encoded by the polynucleotides also inhibit HIV-1 gene expression. The polypeptides and proteins encoded by the aforedescribed isolated polynucleotides in some embodiments may be further defined as having a molecular weight of between about 40 kD and about 46 kD as determined by SDS polyacrylamide gel electrophoresis. One embodiment of the polynucleotide encodes a protein having an amino acid sequence as defined in SEQ ID NO: 1. This particular embodiment of the polynucleotide may be further described as being encoded by a nucleic acid sequence as defined in SEQ ID NO: 2, or fragments thereof, particularly to sequences 276–375, 21–375, 21–498, 21–594, 21–720, 21–999, 21–1242, 21–1263, and 276–945 of SEQ ID NO:2. The polynucleotide may be obtained from the genome of HeLa cells, as well as any other mammalian cell line, particularly a human cell line, that is susceptible to infection by HIV.

As used herein, the terms "polynucleotide" and "DNA segment" are used interchangeably and refer to a DNA molecule which has been isolated free of total genomic DNA of a particular species. Therefore, a "purified" polynucleotide or DNA segment as described herein, refers to a DNA segment which includes a sequence encoding a polypeptide fragment, or full length TDP-43 protein, yet is isolated away from, or purified free from, free total genomic DNA, for example, total human genomic DNA. Included within the term "DNA segment", are DNA segments and smaller fragments of such segments, and also recombinant vectors, including, for example, plasmids, cosmids, phage, viruses, and the like.

One embodiment of the purified polynucleotide of the invention is further defined as having a sequence consisting essentially of a nucleotide sequence in accordance with SEQ ID NO:2. Such nucleotide sequences are more particularly defined as being substantially free of nucleic acids not encoding the cellular binding (TDP-43) protein of a polypeptide fragment thereof.

Similarly, a DNA segment comprising an isolated or purified TDP-43 gene refers to a DNA segment including TDP-43 coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case the TDP-43 encoding gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

The aforedescribed isolated polynucleotide sequences may also be contained within an adenovirus, a retrovirus (see, for example, Morgenstern et al. (1990) Nucleic Acids Research, 18(12):3587–96), or a plasmid. These particular embodiments of the invention would be particularly efficacious in pharmaceutical preparations. By way of example, these preparations of the invention may be used in the treatment of patients with HIV infection.

In particular embodiments, the invention concerns isolated DNA segments and recombinant vectors incorporating DNA sequences that encode a cellular binding protein, the TDP-43 gene, that includes within its amino acid sequence an amino acid sequence in accordance with SEQ ID NO:1, or a fragment of that sequence. Moreover, in other particular embodiments, the invention concerns isolated DNA segments and recombinant vectors incorporating DNA sequences which encode a gene that includes within its amino acid sequence the amino acid sequence of a TDP-43 gene corresponding to human TDP-43.

Another embodiment of the present invention is a purified nucleic acid segment that encodes a protein in accordance with SEQ ID NO:1, further defined as a recombinant vector. As used herein the term, "recombinant vector", refers to a vector that has been modified to contain a nucleic acid segment that encodes a cellular binding protein that binds to HIV LTR DNA, that does not bind TAR RNA, and that inhibits HIV gene expression. These vectors include sequence encoding a TDP-43 protein, or fragments thereof. Particular embodiments of these vectors include a DNA segment encoding a cellular binding protein encoded by an amino acid sequence 7–125, 7–166, 7–198, 7–240, 7–333, 7–414, 7–421, 92–315, 92–125, or a combination thereof of SEQ ID NO: 1. The recombinant vector may be further defined as an expression vector comprising a promoter operatively linked to or adjacent to said cellular binding protein or polypeptide encoding nucleic acid segment. In a particular embodiment, the recombinant vector comprises a nucleic acid sequence in accordance with SEQ ID NO: 2, or a fragment of SEQ ID NO: 2 from position 21–375, 21–498, 21–594, 21–720, 21–999, 21–1242, 21–1263, 276–945, 276–375, or a combination thereof.

In particular embodiments, the recombinant vectors of the invention comprise one or more nucleic acid segments that convey resistance to at least one antibiotic to a whole cell, a vector sequence and a nucleic acid sequence encoding a cellular binding protein or polypeptide that binds to a sequence −18 to +28 of HIV LTR DNA, that does not bind to a sequence +1 to +80 of TAR RNA and that inhibits HIV-1 gene expression.

In further defined embodiments, the aforedescribed recombinant vectors comprise a second nucleic acid sequence encoding a second protein or polypeptide, or even a third, fourth or fifth protein. In such embodiments, the recombinant vector expresses a cellular binding protein or polypeptide fragment thereof as a fusion protein with the second, third, etc. encoded protein or polypeptide. By way of example, such a second nucleic acid sequence may encode for gene 10 or glutathione S-transferase protein. The nucleic acid segment of the recombinant vector encoding the cellular binding protein or polypeptide fragment thereof is further defined as operatively linked to a promoter. Such useful promoters include T7 promoter, maltose promoter and lac 2 promoter. A particular vector employed by the present inventors is the pGEX-2T vector. However, many other vectors may be used in the practice of these embodiments of the invention, as will be readily apparent to those of skill in the art.

A further preferred embodiment of the present invention provides a host cell transformed with a polynucleotide, made recombinant or transformed with a recombinant vector comprising a polynucleotide acid segment having a sequence of SEQ ID NO: 2, or a fragment of that sequence, particularly those fragments defined herein. The recombinant host cell may be a prokaryotic or a eukaryotic cell. In one embodiment, the recombinant host cell is a bacterial cell, such as *E. coli*. However, many other host cells may be used in the practice of the present invention, as will be appreciated by those of ordinary skill in the art. Thus the present invention also includes recombinant hosts or vectors that may be further defined as a *Saccharomyces cerevisiae*, Baculovirus, or Vaccinia virus.

The polynucleotide encoding the binding protein TDP-43 or a polypeptide fragment thereof is in particular embodiments under the transcriptional control of regulatory signals functional in the recombinant host cell. These regulatory signals appropriately control the expression of the cellular binding protein in a manner to allow all necessary transcriptional and post transcriptional modification.

As used herein, the term "engineered" or "recombinant" cell is intended to refer to a cell into which a recombinant gene, such as a gene encoding TDP-43 or a polypeptide thereof, has been introduced. Therefore, engineered cells are distinguishable from naturally occurring cells which do not contain a recombinantly introduced gene. Thus, engineered cells are cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene, or combinations thereof.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired. In a particular aspect, the cDNA encoding the TDP-43 cellular binding protein and polypeptides of the invention bind to a sequence −18 to +28 of HIV LTR DNA, do not bind a sequence +1 to +80 of TAR RNA, and inhibit (represses) HIV gene expression. The particular nucleic acid sequence may be defined in one embodiment of the cDNA as having a sequence essentially as set forth at position 21 to nucleic acid position 1263 of SEQ ID NO: 2.

In addition to the methods above for obtaining cell-derived forms of TDP-43 protein, the present invention also provides methods for producing a recombinant form of the cellular binding protein, TDP-43, and polypeptides thereof. In a particular embodiment, the method comprises growing cells transformed with a nucleic acid sequence encoding a cellular binding protein or polypeptide that binds with specificity to a sequence −18 to +28 of HIV LTR DNA, that does not bind sequence +1 to +80 of TAR RNA, and that represses or otherwise inhibits HIV-1 gene expression. Such transformed cells are grown in a nutrient medium suitable for the expression of the cellular binding protein. By way of example, such a suitable nutrient medium for the expression of the cellular binding protein is tryptone broth. The cells employed for providing the recombinant cellular binding protein are preferably bacterial cells. By way of example, such bacterial cells are *E. coli*. In one aspect, the cells are transformed with a nucleic acid sequence essentially as set forth in SEQ ID NO: 2, or a fragment thereof, such as the fragment 21–1242 of SEQ ID NO:2.

In some embodiments of the invention, nucleic acid sequences that encode a fusion protein of the cellular binding protein or polypeptide thereof together with a second protein, such as glutathione S-transferase (GST-TDP-43 fusion protein) or gene 10 protein, are provided. Once expressed as a fusion protein, the sequence encoding the cellular binding protein or polypeptide thereof may be isolated apart from the product of the second encoded protein, by for example, thrombin cleavage of the GST-TDP-43 fusion protein. Particular truncated polypeptides of TDP-43 protein are described in examples herein.

The aforedescribed methods may further comprise the step of isolating the express cellular binding protein or polypeptide. Several techniques for isolating expressed proteins from a culture of recombinant cells are known to those of skill in the art, and may be employed in the practice of the present method as well.

The term "a sequence essentially as set forth in SEQ ID NO:1" or "NO: 2" means that the sequence substantially corresponds to a portion of SEQ ID NO:1, or SEQ ID NO: 2, and has relatively few amino acids or nucleic acids that are not identical to, or a biologically functional equivalent of, the amino acids of SEQ ID NO:1 or nucleic acids of SEQ ID NO: 2. The term "biologically functional equivalent" is well understood in the art and is further defined in detail herein, as a gene encoding a sequence essentially as set forth in SEQ ID NO:1 or NO: 2, and that is associated with binding to the viral TAR DNA region of HIV. Accordingly, sequences which have between about 70% and about 80%; or more preferably, between about 81% and about 90%; or even more preferably, between about 91% and about 99%; of amino acids or nucleic acids which are identical or functionally equivalent to the amino acids or nucleic acids of SEQ ID NO:1 will be sequences which are "essentially as set forth in SEQ ID NO:1."

The term "essentially as set forth", in reference to nucleic acid sequence positions in SEQ ID NO:2, is used in the same sense as described above and means that the nucleic acid sequence substantially corresponds to a portion of SEQ ID NO:2, and has relatively few codons which are not identical, or functionally equivalent, to the codons of SEQ ID NO:2. The term "functionally equivalent codon" is used herein to refer to codons that encode the same amino acid, such as the six codons for arginine or serine, as set forth in Table 1, and also refers to codons that encode biologically equivalent amino acids.

TABLE 1

CODON DEGENERACY

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

It will also be understood that amino acid and nucleic acid sequences may include additional residues, such as additional amino- or carboxy-terminal amino acids or 5' or 3' sequences, and yet still be essentially as set forth in one of the sequences disclosed herein, so long as the sequence meets the criteria set forth above, including the maintenance of biological protein or polypeptide activity where protein or polypeptide expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:2 will be sequences which are "essentially as set forth in SEQ ID NO:2". Sequences which are essentially the same as those set forth in SEQ ID NO:2 may also be functionally defined as sequences which are capable of hybridizing to a nucleic acid segment containing the complement of SEQ ID NO:2 under relatively stringent conditions. Suitable relatively stringent hybridization conditions will be well known to those of skill in the art and are clearly set forth herein, for example, conditions for use with Northern Blot analysis, and as described in the preferred embodiments and in Example 2.

Naturally, the present invention also encompasses DNA segments which are complementary, or essentially complementary, to the sequence set forth in SEQ ID NO:2 or its fragments. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:2 under relatively stringent conditions such as those described herein in the detailed description of the preferred embodiments.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be encompassed which include a short stretch complementary to SEQ ID NO: 1, such as about 30 to 140 or 150, 160, 170, 180, or 200, 250, 300 or 400 or so nucleotides, and that are up to 500 or 1,000 base pairs in length, with segments of about 1,300 being preferred in certain cases. DNA segments with total lengths of about 500, 700, or 900 and about 1263 base pairs in length are also contemplated to be useful.

One embodiment of the present invention constitutes a nucleic acid segment which comprises an about 300 to 1,300 nucleotide long stretch which corresponds to, or is complementary to, a portion of the nucleic acid sequence of SEQ ID NO:2. In particularly defined embodiments, the nucleic acids of the invention are further defined as a 414 polynucleotide, a 477 polynucleotide, a 573 polynucleotide, a 699 polynucleotide, a 888 polynucleotide, a 1,221 polynucleotide, a 1,242 polynucleotide, or a 1269 polynucleotide length cDNA that is complementary to a segment of the nucleic acid sequence of SEQ ID NO:2.

A related embodiment of the present invention is a nucleic acid segment which comprises a between about 300 nucleotide and about 3,000 nucleotide segment which corresponds to, or is complementary to, a portion of the nucleic acid sequence of SEQ ID NO: 2. A more preferred embodiment is a nucleic acid fragment comprising from 100–200 nucleotides of SEQ ID NO:2, or up to 800 basepairs in length, 600 basepairs in length, 400 basepairs in length, 300 basepairs in length, or 200 basepairs in length.

Naturally, it will also be understood that this invention is not limited to the particular amino acid and nucleic acid sequences of SEQ ID NOS:1 and 2. Recombinant vectors and isolated DNA segments may therefore variously include the TDP-43 and polypeptide coding regions themselves, coding regions bearing selected alterations or modifications in the basic coding region, or they may encode larger polypeptides which nevertheless include TDP-43-coding regions or may encode biologically functional equivalent proteins or peptides which have variant amino acids sequences.

The DNA segments of the present invention encompass biologically functional equivalent TDP-43 proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the TDP-43 protein a polypeptide or to test TDP-43 mutants in order to examine viral TAR DNA region binding promoting activity and potential at the molecular level.

The term "purified" as used herein, is intended to refer to a TDP-43 protein composition, wherein the TDP-43 protein is purified to any degree relative to its naturally-obtainable state, i.e., in this case, relative to its purity within a eukaryotic cell nuclear extract. A preferred cell for the isolation of TDP-43 protein is a HeLa cell, however, TDP-43 protein may also be isolated from recombinant cells, tissues, isolated subpopulation of tissues, and the like, as will be known to those of skill in the art, in light of the present disclosure. A purified TDP-43 protein composition therefore also refers to a polypeptide having the amino acid sequence of SEQ ID NO:1 or a fragment thereof, free from the environment in which it may naturally occur.

If desired, one may also prepare fusion proteins or truncated proteins and peptides, e.g., where the TDP-43 coding regions, or fragments thereof, are aligned within the same expression unit with other proteins or peptides having desired functions, such as for purification or immunodetection purposes (e.g., proteins which may be purified by affinity chromatography and enzyme label coding regions, respectively). Particular embodiments of these truncated and fusion proteins and peptides are, again, discussed in the examples.

Turning to the expression of the TDP-43 gene whether from cDNA based or genomic DNA, one may proceed to prepare an expression system for the recombinant preparation of TDP-43 protein. The engineering of DNA segment(s) for expression in a prokaryotic or eukaryotic system may be performed by techniques generally known to those of skill in recombinant expression. For example, a TDP-43-GST (glutathione-S-transferase) fusion protein construct provides a convenient means of bacterial expression. However, it is believed that virtually any expression system may be employed in the expression of TDP-43.

TDP-43 may be successfully expressed in eukaryotic expression systems. In one example, the inventors have used bacterial expression systems for the preparation of recombinant TDP-43 for all purposes. The cDNA for TDP-43 may be separately expressed in bacterial systems, with the encoded proteins being expressed as fusions with glutathione transferase or gene 10 protein. Other proteins that may be employed include β-galactosidase, avidin, ubiquitin, *Schistosoma japonicum* glutathione S-transferase, epitope-tags and the like. It is believed that bacterial expression will ultimately have advantages over eukaryotic expression in terms of ease of use and quantity of materials obtained thereby. The present inventors employing the herein disclosed techniques and materials, can obtain about 1 mg of the TDP-43 protein per liter of bacterial culture.

It is proposed that transformation of host cells with DNA segments encoding the TDP-43, or polypeptides thereof, will provide a convenient means for obtaining a TDP-43 protein or truncated protein. It is also proposed that cDNA, genomic sequences, and combinations thereof, are suitable for eukaryotic expression, as the host cell will, of course, process the genomic transcripts to yield functional mRNA for translation into protein.

Another aspect of the invention provides a method of preparing a recombinant TDP-43 protein composition comprising growing recombinant host cells comprising a vector that encodes a protein which includes an amino acid sequence in accordance with SEQ ID NO:1, under conditions permitting nucleic acid expression and protein production followed by recovering the protein so produced. The host cell, conditions permitting nucleic acid expression, and protein production and recovery, will be known to those of skill in the art, in light of the present disclosure of the TDP-43 gene.

It is similarly believed that almost any eukaryotic expression system may be utilized for the expression of TDP-43 and its polypeptide fragments, e.g., baculovirus-based, glutamine synthase-based, dihydrofolate reductase-based systems, or the like, could be employed. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the TDP-43 gene, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of TDP-43 in accordance herewith. Examples include cell lines typically employed for eukaryotic expression such as 239, AtT-20, HepG2, VERO, HeLa, Jurkat, CHO, WI 38, BHK, COS-7, RIN and MDCK cell lines.

In yet another embodiment, the present invention provides for a method of detecting a nucleic acid species that is capable of hybridizing to a nucleic acid segment in accordance with SEQ ID NO:2. The method for detecting the nucleic acid species comprises the steps of obtaining a nucleic acid sample and contacting the sample with a nucleic acid segment in accordance with SEQ ID NO:2 under conditions effective to allow hybridization to form a complex. As used herein, the phrase "obtaining a nucleic acid sample" is used to describe nucleic acid samples located both within intact cells, for example, a cell sample for in situ hybridization, and of nucleic acids that have been isolated away from cells. Naturally, it is understood that nucleic acids encompass the multiple forms of RNA as well as DNA samples, and are isolatable as described above, and as known to those of skill in the art in light of the present disclosure. In one embodiment, the nucleic acid segment comprises a detectable label that is enzymatic-, fluorescent-, or radio-, or chemiluminescently-labelled.

Those of skill in the art will, in light of the present disclosure, be able to label TDP-43 coding nucleic acid sequences, or polypeptide fragments of the TDP-35, for detection. Techniques for use in the detection of nucleic acids, such as, in situ hybridization, Southern and Northern blotting, pulse-field gel electrophoresis, nuclease protection assays, unbolts, and the like, will be known to those of skill in the art, in light of the present disclosure. The "conditions effective to allow" nucleic acid hybridization, will also be known to those of skill in the art, and as disclosed herein in particular embodiments, and as described in Sambrook et al. (1989).

A target nucleic acid for use in a method of detecting the polypeptides and TDP-43 of the present invention, are target DNAs that bind TDP-43 when located within a cell. The detection of DNAs that bind TDP-43 found within cells is accomplished by binding of the protein to the DNA and analyzing the bound complex on a gel, referred to as a gel retardation assay. The cells for use with gel retardation may be isolated from a solid tumor, a dispersed tumor, or from cells grown in tissue culture.

In an alternative embodiment, the target nucleic acids are separated from the cell prior to contact. A wide variety of methods for isolating target nucleic acids are contemplated, such as cesium chloride gradient centrifugation, chromatography (ion, affinity, magnetic), phenol extraction, and the like. Furthermore, the isolated target nucleic acids can be detected following electrophoretic separation and immobilization onto a solid matrix, as is the case with Southern, Northern, and pulse-field electrophoresis, or directly in gel as in the case of unbolts. The nucleic acids may also be contacted prior to electrophoretic separation as in the case of nuclease protection assays.

Antibodies

In another aspect, the present invention contemplates an antibody that is immunoreactive with a polypeptide of the invention. An antibody can be a polyclonal or a monoclonal antibody. In one embodiment, the antibody is a polyclonal antibody. Means for preparing and characterizing antibodies are well known in the art. Particular references such as Howell, E. and D. Lane, 1988, are specifically incorporated herein for this purpose.

Briefly, a polyclonal antibody is prepared by immunizing an animal with an immunogen comprising a polypeptide of the present invention and collecting antisera from that immunized animal as demonstrated in Example 3. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the TDP-43 of the present invention may be prepared using conventional immunization techniques, as will be generally known to those of skill in the art. A composition containing antigenic epitopes of the TDP-43 sequences, isolated TDP-43, or fragments thereof can be used to immunize one or more experimental animals, such as a rabbit or mouse, which will then proceed to produce specific antibodies against TDP-43. Polyclonal antisera may be obtained, after allowing time for antibody generation, simply by bleeding the animal and preparing serum samples from the whole blood. In one embodiment, the antibody is a polyclonal antibody that binds to a TDP-43 cellular binding protein having a molecular weight of between about 40 and about 46 kD as determined by SDS polyacrylamide gel electrophoresis, said TDP-43 cellular binding to a sequence −18 to +28 of HIV LTR DNA and not binding TAR RNA.

In one particular embodiment, the method comprises administering a mixture comprising a fusion protein of the cellular binding protein that binds TAR DNA, does not bind TAR RNA and inhibits HIV gene expression, and a second protein, in Freund's adjuvant to an animal; administering a second mixture of the fusion protein to the animal, and recovering the antibody to the TDP-43 cellular binding protein from biological fluid of the animal. In a preferred embodiment, the mixture which is used to immunize the animal includes a cellular binding protein encoded by an amino acid sequence of amino acids 92 to 315 of SEQ ID NO: 1. In a particular aspect, the fusion protein comprises the aforedescribed amino acid fragment encoded polypeptide and glutathrone S-transferase or gene 10. The method may further comprise a step of purifying antibody that binds the TDP-43 cellular protein or the aforedescribed fusion protein that includes a polypeptide fragment of TDP-43, from the biological fluid of the animal.

To obtain monoclonal antibodies, one would also initially immunize an experimental animal, often preferably a mouse, with a purified TDP-43 composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired TDP-43 protein or polypeptide of TDP-43.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against TDP-43. Hybridomas which produce monoclonal antibodies to the selected antigens are identified using standard techniques, such as ELISA and Western Blot methods.

Hybridoma clones can then be cultured in liquid media and the culture supernatants purified to provide the TDP-43-specific monoclonal antibodies. In general, monoclonal antibodies to the TDP-43 antigen can be used in both the diagnosis and treatment of HIV infections. In such uses of the antibody, decreased expression of the protein in a biological sample may be monitored to trace the progression of HIV disease. Alternatively, the antibody may be used to determine the amount of TDP-43 protein in a sample, such as in a blood serum sample. The protein itself may also be used as a molecular weight marker, as it is characterized herein as having a molecular weight of 43 kD. It is proposed that the monoclonal antibodies of the present invention will find useful application in standard immunochemical procedures, such as ELISA and Western blot methods, as well as other procedures which may utilize antibody specific to common or allelically distinct TDP-43 epitopes. These TDP-43-specific monoclonal antibodies are anticipated to be useful in various ways for the treatment of TDP-43 infections through, for example, their application in immunodetection procedures.

Additionally, it is proposed that monoclonal antibodies specific to the particular TDP-43 may be utilized in other useful applications. For example, in immunoabsorbent protocols, they may be useful in purifying native or recombinant TDP-43 species or variants thereof.

In general, both poly- and monoclonal antibodies against TDP-43 may be used in a variety of embodiments. For example, they may be employed in antibody cloning protocols to obtain cDNAs or genes encoding related proteins. They may also be used in inhibition studies to analyze the effects of TDP-43 in cells or animals. Anti-TDP-43 antibodies will also be useful in immunolocalization studies to analyzes the distribution of TDP-43 during various cellular events, for example, to determine the intracellular localization and distribution of TDP-43 during the presence or absence of HIV infection, as well as during disease progression. A particularly useful application of such antibodies is in purifying native or recombinant TDP-43, for example, using an antibody affinity column. The operation of all such immunological techniques will be known to those of skill in the art in light of the present disclosure.

Immunoassay

The present invention, in still another aspect, defines an immunoassay for the detection of an antibody specific for a DNA binding element TDP-43 in a biological sample. In one particular embodiment, the immunoassay comprises; preparing a cellular binding protein specific for TAR DNA and which regulates HIV gene expression to provide a TDP-43 antigen, incubating the TDP-43 antigen with the biological sample for a sufficient time to permit binding between antigen and antibody present in said biological sample, and determining the presence of bound antibody by contacting the incubate of the antigen and antibody with a detectably labeled antibody specific for the anti-TDP-43 antibody, wherein the presence of anti-TDP-43 antibody in the biological sample is detectable as the measure of the detectably labeled antibody from the biological sample.

By way of example, the antibody may be labeled with any of a variety of detectable molecular labeling tags. Such include, an enzyme-linked (alkaline phosphatase) antibody, a fluorescent-tagged antibody, or a radio-labelled antibody. In one particular embodiment of the described immunoassay, the TDP-43 is prepared from mammalian cell nuclei is obtained from a recombinant host expressing said TDP-43 antigen.

In still another embodiment of the invention, a hybridoma cell line which produces a monoclonal antibody which specifically binds a TDP-43 cellular protein is provided. Most particularly, the hybridoma cell line is a murine hybridoma cell line produced by immunizing a mouse or a rat with a cellular protein TDP-43 which binds an HIV TAR DNA, isolating anti-TDP-43 antibody producing cells from the immunized mouse, and fusing the antibody producing cells with a neo-plastic murine cell line to obtain a murine hybridoma cell line.

Pharmaceutical Preparations

Another aspect of the present invention provides a therapeutic agent for the treatment of HIV or HTLV infection in an animal. By way of example, the therapeutic agent of the invention may take the form of antisense oligonucleotide that bind to the pyrimidine rich regions of the HIV LTR DNA described herein as characteristic of the TDP-43 protein. This would provide a repression of HIV gene expression, thus halting the disease. These antisense oligonucleotides would be fashioned according to techniques known to those of skill in the art using the sequence specific binding region information (i.e., the pyrimidine regions of the HIV LTR DNA) disclosed herein.

The protein and polypeptides of the invention may in some embodiments be orally administered, for example, with an inert diluent or with an assimilable edible carrier, or they may be enclosed in hard or soft shell gelatin capsule, or they may be compressed into tablets, or they may be incorporated directly with the food of the diet. For oral administration, the compounds may be incorporated with excipients and used in the form of ingestible tablets, buccal tables, troches, capsules, elixirs, suspensions, syrups, wafers, and the like. Such compositions and preparations should contain at least 0.1% of the TDP-43 protein or polypeptide. The percentage of the compositions and preparations may, of course, be varied and may conveniently be between about 2 to about 60% of the weight of the unit. The amount of the TDP-43 protein or polypeptide in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the protein or polypeptide may be incorporated into a sustained-release preparation or formulation.

The proteins and polypeptides may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

DNA Binding Complex

In still another aspect of the present invention, an DNA binding complex is provided. The DNA binding complex may be particularly useful in characterizing the molecular events of HIV gene expression. In one particular embodiment, the DNA binding complex comprises the TDP-43 cellular protein capable of binding a TAR DNA region of HIV, and a volume of TAR DNA sufficient to bind the TDP-43.Most preferably, the TDP-43 cellular protein is isolated from a HeLa cell nuclear cell extract as previously described hereinabove. It is anticipated that the described DNA binding complex may be used as a laboratory and candidate substance screening reagent, most particularly in the characterization of viral and cellular gene expression, and inhibitors thereof. The DNA binding complex may also be used to screen for factors that would enhance the ability of TDP-43 to compete with TAT, thus providing for even further improved activity for repressing (inhibiting) HIV gene expression according to the present invention.

Assays for Candidate Substances

In still further embodiments, the present invention concerns a method for identifying new TDP-43-TAR DNA binding proteins and polypeptides, which may be termed as "candidate substances" having an expected activity of that of the TPP-43 cellular protein. It is contemplated that this screening technique will prove useful in the general identification of any compound that will serve the purpose of binding the HIV-1 LTR DNA region described herein, that further selectively does not bind TAR RNA. It is further contemplated that useful compounds will in no way be limited to proteinaceous or peptidyl compounds.

Accordingly, in screening assays to identify pharmaceutical agents that inhibit HIV gene expression, it is proposed that compounds isolated from natural sources such as plants, animals or even sources such as marine, forest or soil samples, may be assayed for the presence of potentially useful pharmaceutical agents. It will be understood that the pharmaceutical agents to be screened could also be derived from chemical compositions or man-made compounds. In important aspects, the candidate substances may be anti-TDP-43 antibodies, including polyclonal and monoclonal antibodies. The suspected agents could also include proteins and peptides, such as those derived from recombinant DNA technology or by other means, including peptide synthesis. The active compounds may include fragments or parts of naturally-occurring compounds or may be only found as active combinations of known compounds which are otherwise inactive.

In these embodiments, the present invention is directed to a method for determining the ability of a candidate substance to inhibit HIV gene expression the method including generally the steps of:

(a) obtaining a DNA binding complex comprising a TDP-43 protein and a TAR DNA sequence;
(b) admixing a candidate substance with the DNA binding complex in the presence of TDP-43; and
(c) determining the ability of the DNA binding complex to bind in the presence of the candidate substance.

An important aspect of the candidate substance screening assay of the present invention is the ability to prepare a native or recombinant TDP-43 composition in a relatively purified form, for example, in a manner as discussed above. This is an important aspect of the candidate substance screening assay in that without at least a relatively purified preparation, one will not be able to assay specifically for the effects of TDP-43, as opposed to the effects of the inhibition by other substances in the extract which then might affect the binding. The successful isolation of the TDP-43 protein will allow for the identification of new compounds which can be used for stimulating the binding of TDP-43 to HIV-1 regions described herein or binding to regions that are complimentary to the regions that TDP-43 binds to.

After obtaining a relatively purified preparation of the TDP-43, either from native or recombinant sources, one will desire to simply admix a candidate substance with the TDP-43 TAR DNA or DNA sequence containing preparation, preferably under conditions which would allow the TDP-43 to perform its binding function but might stimulate the binding. One can measure the ability of the candidate substance to inhibit HIV-1 gene expression.

Any method may generally be employed to determine TDP-43 protein binding to TAR nucleic acid sequences. Preferred methods will be those in which the target TAR coding nucleic acids incorporates, or is conjugated to, a label, such as an enzymatic, chemical or radiolabel, or incorporates one of the ligands of a two ligand-based detection system such as the avidin/biotin system. For ease and safety, the use of enzymatic labels, such as, for example, horse radish peroxidase, urease or alkaline phosphatase is preferred. In such cases, a colorimetric indicator substrate would be employed to provide a means visible to the human eye, or spectrophotometrically, to identify specific hybridization with labelled target sequences.

In still further embodiments, the present invention is concerned with a method of inhibiting basal and TAT induced gene expression that includes subjecting a DNA binding complex to an effective concentration of a candidate inhibitor such as one of the family of protein or non-proteinaceous compounds discussed above, or with a candidate substance identified in accordance with the candidate screening assay embodiments. This is, of course, an important aspect of the invention in that it is believed that by TAR nucleic acid sequences, one will be enabled to treat various aspects of retroviral infection, including the HIV virus and related members of the Lentivirus family. It is believed that the use of such will serve to treat cells that can be, or have already been infected with a retrovirus, such as HIV, and may be useful by themselves or in conjunction with other therapies, including the use of nucleic acid homologs and the like.

Test Pack

In still another embodiment, a diagnostic test pack for the detection of anti-TDP-43 antibody in a biological sample is provided. Alternatively, the test pack may be fashioned to measure levels of the TDP-43 protein in a sample, such as a blood serum sample.

In one embodiment, the diagnostic test pack comprises in packaged combination a carrier means adapted to receive at least three container means in close confinement therewith, a first container means including a TDP-43 cellular protein or polypeptide capable of binding a TAR DNA (or the TDP-43 cellular binding protein itself having molecular weight of about 43 kD), a second container means including a quantity of an unlabeled antibody having specific binding affinity for the TDP-43 cellular protein or polypeptide, a third container means including a quantity of a detectably labeled antibody specific for binding with the anti-TDP-43 antibody, and at least one microtiter plate.

More specifically, the detectably labeled antibody of the described test-pack is an enzyme-linked antibody, a fluorescent tagged antibody or a radio-labeled antibody. By way of example, radiolabels such as $^{125}I$, $^{3}H$ and others may be used to label the antibody.

The test pack in still another embodiment may include a fourth container means having a quantity of a substrate for the enzyme sufficient to produce a visually detectable product, where the antibody of choice is an enzyme-linked antibody. Even more preferably, the antibodies of the diagnostic text pack are monoclonal antibodies specific for the TDP-43 cellular protein. Alternatively, both the unlabeled antibody and the detectably labeled antibody are polyclonal antibodies specific for the TDP-43 cellular protein.

In particular embodiments of the described therapeutic agents, "inhibitors" of TDP-43 may, in addition to the aforedescribed specific antibodies for TDP-43, include antisense DNA, such as, for example, a DNA fragment that preferentially binds the TAR DNA region between nucleotides −18 to +28 in the HIV-1 LTR.

In the aforedescribed method for obtaining the TDP-43 binding protein, preparing a nuclear extract from mammalian cells may be more generically described as disrupting the integrity of these cells and obtaining the nuclei and then disrupting the integrity of the nuclei and using the soluble proteins which bind to TAR DNA in the following steps. Similarly, the steps for fractionating the nuclear extract as described as part of the claimed methods may be more generically described as binding the nuclear extracts to a chromatography column (i.e., phosphocellulose) and eluting with specific concentrations of KCL or other suitable buffer, dialyzing the proteins contained in the different column fractions eluted from the chromatography column, identifying column fractions which contain protein or polypeptide that binds to TAR DNA using gel retardation analysis, repeating the procedure of binding to different columns containing either cationic or anionic resins, followed by elution, and assaying the fractions using TAR DNA gel retardation. Chromatography columns that may be used sequentially after the phosphocellulose column include hydroxyapatite, Biogel, Superdex 20 fast phase liquid chromatography (FPLC), Bio-Rex, Dextran Blue Sepharose, heparin agarose and a mono Q FPLC.

The present invention also provides for methods for inhibiting HIV gene expression comprising administering to cells infected with human immuno deficiency virus a preparation comprising a TDP-43 cellular binding protein or polypeptide that binds to a TAR region of HIV LTR DNA, that does not bind TAR RNA, and that inhibits HIV gene expression. In one embodiment, the method employs a TDP-43 cellular binding protein defined as having a molecular weight of about 40 kD to about 46 kD as determined by SDS polyacrylamide gel electrophoresis. In a preferred aspect of the described method, the TDP-43 cellular binding protein is encoded by an amino acid sequence essentially as set forth in SEQ ID NO: 1. Alternatively, the method comprises administering a retrovirus or adenovirus that includes a nucleic acid sequence encoding the cellular binding protein TDP-43 or a polypeptide thereof, to infected cells. In one embodiment, the sequence included in the retrovirus or adenovirus is essentially as set forth in the nucleic acid sequence at SEQ ID NO: 2, or the particularly defined fragments thereof defined herein.

Lastly, the present invention provides methods for detecting a nucleic acid sequence that hybridizes to a nucleic acid segment essentially as set forth in SEQ ID NO: 2. In one embodiment, the method comprises obtaining a nucleic acid sample and contacting the sample with a nucleic acid segment in accordance with SEQ ID NO: 2 (or a fragment thereof as described) under conditions sufficient to allow hybridization to form a complex. This method may be useful in a variety of applications, particularly in screening for other nucleic acid sequences that may provide the same inhibitory activity for HIV-1 gene expression as those sequences specifically disclosed herein.

Following long-standing patent law convention, the terms "a" and "an" is intended by the present inventors to mean "one or more" when used in the description of the present inventions of this application, including the claims.
Model of TDP-43 Repression of HIV-1 Gene Expression The present inventors have also determined the association of the TATA binding protein (TBP), TATA associated factors (TAFs), general transcription factors (GTFs), and RNA polymerase II and associated factors (RNA Pol II) to the HIV-1 promoter. During basal gene expression of the HIV-1 promoter, there is a block to transcriptional initiation and elongation which is relieved by Tat. The present of TDP-43 decreases the number of functional transcription initiation complexes that are assembled by steric effects resulting in decreased basal (B) and Tat-induced gene expression (D). Thus, the mechanism of transcriptional repression of HIV-1 gene expression by TDP-43 may be explained by its ability to block the assembly of a transcriptional initiation complex that is competent to respond to Tat.
Site Selection of Oligonucleotides Using Recombinant TDP-43

Using site selection and the recombinant TDP-43 sequences disclosed herein, the present inventors identified particular oligonucleotides. Random oligonucleotides with unique 5' and 3' termini and 35 random internal nucleotides were incubated with recombinant TDP-43 followed by immunoprecipitation with rabbit polyclonal antibody directed against TDP-43. PCR analysis was performed with oligonucleotides complementary to the 5' and 3' termini followed by five additional cycles of binding, immunoprecipitation, and PCR amplification of the DNA that coimmunoprecipitated with TDP-43 antibody. The amplified oligonucleotides were cloned into an AT cloning vector (Invitrogen), twenty-one unique clones were analyzed by DNA sequence analysis, and similar sequences were aligned. The common feature of these PCR products was the presence of at least eight contiguous pyrimidine residues containing alternating groups of cytidine and thymidine. A comparison of these sequences with that of TAR DNA reveals homology with two sets of pyrimidine-rich sequences in the HIV-1 LTR between −15 and −5 and +4 and +11.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows a variety of carboxy-terminal truncations of TDP-43 fused to the glutathione S-transferase protein are schematically shown.

Figure 1:
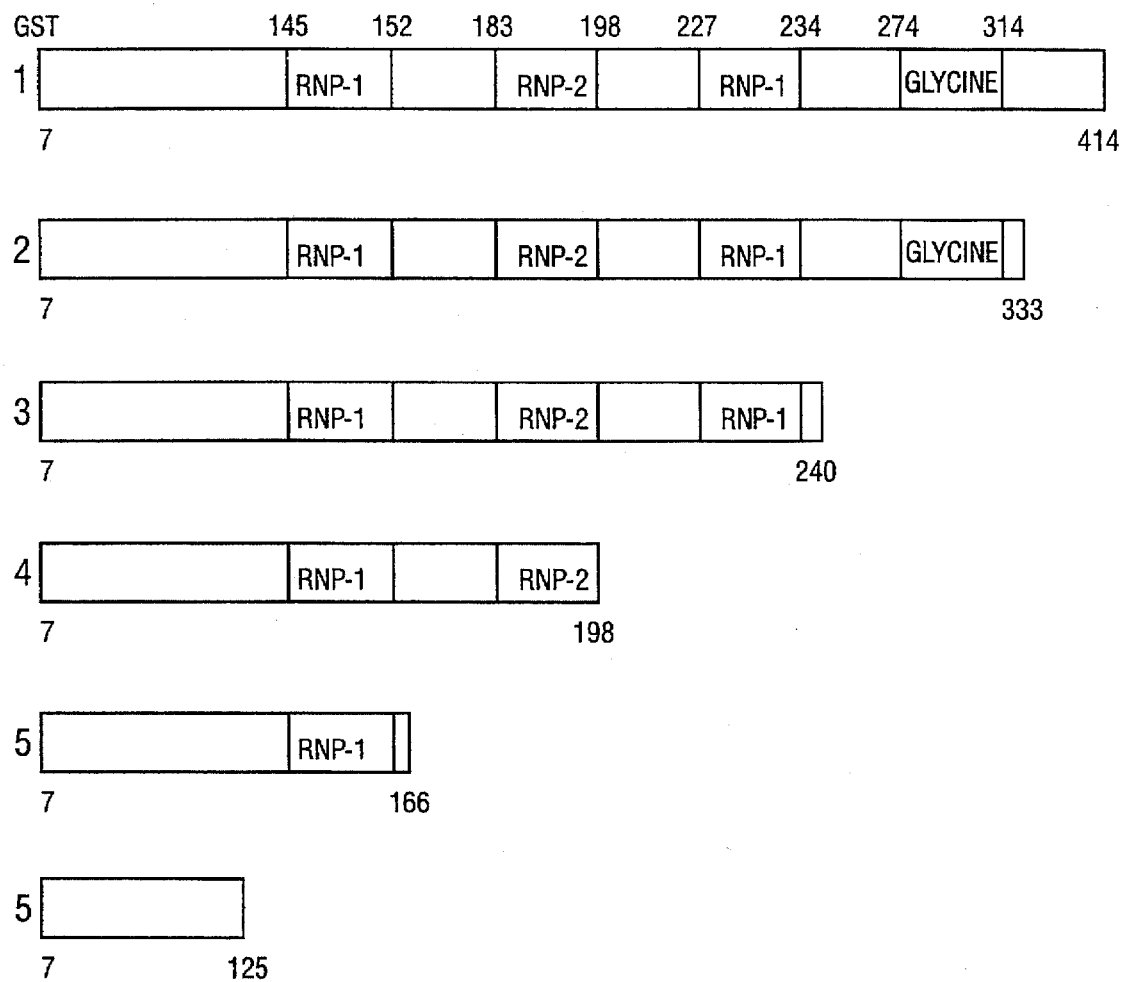
FIG. 1 shows analysis of domains in TDP-43 required for its DNA binding properties.

One day prior to transfection, $3 \times 10^5$ HeLa cells were seeded onto 60 mm plates. When the plates were 50–70% confluent they were co-transfected with a wild type HIV-1 proviral molecular clone and an RSV based eucaryotic vector expressing either TDP-43, ΔTDP-43 that expresses only the first 95 amino acids of TDP-43, the first intron of rabbit β-globin gene, or the parental expression vector. Each transfection included an RSV-β-galactosidase vector to control for transfection efficiency. On day 3 and day 6, 0.5 ml of culture supernatant was assayed for p24 antigen by ELISA and the results were normalized to reflect the actual transfection efficiency as determined by cell staining for β-galactosidase on day 6. Each transfection was performed three times and the results include the standard deviation for the three experiments.

DETAILED DESCRIPTION OF THE PREFERRED EMBODIMENTS

The present invention provides cellular factor polypeptides and full length proteins that bind to TAR DNA. The polypeptides and proteins were obtained by using a portion of TAR DNA extending from −18 to +28 to probe a HeLa cDNA expression library cloned into λgt11. The present inventors identified a cDNA that encodes a cellular factor of 43 kDa, designated TAR DNA Binding Protein (TDP-43), that binds specifically to pyrimidine-rich motifs in TAR DNA. Antibody to TDP-43 was used in gel retardation assays to demonstrate that endogenous TDP-43, present in HeLa nuclear extract, also bound to TAR DNA. Though TDP-43 bound strongly to double-stranded TAR DNA via its ribonucleoprotein binding motifs, it did not bind to TAR RNA extending from +1 to +80. In vitro transcription analysis demonstrated that TDP-43 repressed in vitro transcription from the HIV-1 LTR in both the presence and absence of Tat, but it did not repress transcription from other promoters such as the adenovirus major late promoter. These results indicate that TDP-43 modulates the level of HIV-1 gene expression by either altering or blocking the assembly of transcription complexes that are capable of responding to Tat.

In its broadest embodiment, the invention provides a polypeptide with HIV DNA binding activity, particularly, to a viral DNA segment of the LTR HIV DNA. More specifically, the binding polypeptide, designated herein binds to HIV DNA at a region defined as the TAR region from about nucleotides −18 to +28. In binding to this region of TAR DNA, the polypeptide represses initiation of transcription from the LTR region of TAR and, therefore, represses gene expression of HIV. Thus, the binding protein, TDP-43, and polypeptides thereof that include these binding regions, may be employed to regulate the level of HIV gene transcription and, therefore, the level of HIV viral activity.

The binding protein of the invention may also be regulating cellular genes. While the specific mechanism/function of the protein (TDP-43) in normal cellular gene function is not exactly known, the fact that the protein is cellular and is known to regulate other gene expression (i.e. binding to vital DNA and regulating viral genes) makes probable its role in regulation of cellular genes. The TDP-43 protein may be (in its nonactivated state) bound to an DNA but be able to move and attach to a variety of DNAs. The TDP-43 protein may thus constitute a critical factor in cellular growth control. Thus, the TDP-43 binding proteins and polypeptides of the present invention may constitute a reagent useful in the study of nucleic acid binding activity and gene expression, such as HIV regulation and expression, and for identifying potential substances that affect these events, thereby regulating TAR region activation.

Nucleic Acid Hybridization

The DNA sequences disclosed herein will also find utility as probes or primers in nucleic acid hybridization embodiments. As such, it is contemplated that oligonucleotide fragments corresponding to the sequence of SEQ ID NO:2 for stretches of between about 10 nucleotides to about 20 or to about 30 nucleotides will find particular utility, with even longer sequences, e.g., 25, 40, 50, 100, 200, 300, 400, 500, 600, 700, 1,000, even up to full length, being more preferred for certain embodiments. The ability of such nucleic acid probes to specifically hybridize to TDP-43-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100, 200, 500, 600, 800, 900, or 1,000 nucleotides or so, complementary to SEQ ID NO:2 will have utility as hybridization probes. These probes will be useful in a variety of hybridization embodiments, such as Southern and Northern blotting in connection with analyzing the role of TDP-43 in HIV activation. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, or even up to the full length of the cDNA as shown in SEQ ID NO:2 according to the complementary sequences one wishes to detect.

The use of a hybridization probe of about 20 nucleotides in length allows the formation of a duplex molecule that is both stable and selective. Molecules having complementary sequences over stretches greater than 20 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 30 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of TDP-43 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating TDP-43, and TDP-43-like genes.

Of course, for some applications, for example, where one desires to prepare mutants employing a mutant primer strand hybridized to an underlying template or where one seeks to isolate TDP-43-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 or 40 amino acids in length are contemplated to be particularly useful, as are DNA segments encoding the entire TDP-43 protein. DNA segments encoding peptides will generally have a minimum coding length in the order of about 45 to about 150, or to about 90 nucleotides. DNA segments encoding full length proteins may have a minimum coding length in the order of about 1263 nucleotides for a protein in accordance with SEQ ID NO:1.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular amino acid and nucleic acid sequences of SEQ ID NO:1 and SEQ ID NO:2, respectively. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding a TDP-43 gene may be introduced into recombinant host cells and employed for expressing a TDP-43 structural or related protein. Alternatively, through the application of genetic engineering techniques, subportions or derivatives of the TDP-43 gene may be employed. Equally, through the application of site-directed mutagenesis techniques, one may re-engineer DNA segments of the present invention to alter the coding sequence, e.g., to introduce improvements to the antigenicity of the protein or to test TDP-43 mutants in order to examine TAR binding activity at the molecular level. Where desired, one may also prepare fusion peptides, e.g., where the TDP-43 coding regions are aligned within the same expression unit with other proteins or peptides having desired functions, such as for immunodetection purposes (e.g., enzyme label coding regions).

Pharmaceutical Preparations

Aqueous compositions (inocula) identified as candidate substance during the screen provided by the present invention may comprise an effective amount of the agent dissolved or dispersed in a pharmaceutically acceptable aqueous medium. Such compositions are also referred to as inocula. The phrase "pharmaceutically acceptable", as used herein, refers to molecular entities and compositions that do not produce an allergic or similar untoward reaction when administered to a human.

The preparation of an aqueous composition that contains a protein or proteoglycan as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A proteoglycan can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Multiple Cellular Factors Bind to TAR DNA

The present example provides data demonstrating that multiple cellular factors bind to TAR DNA.

To identify different cellular proteins that can potentially bind to TAR DNA, UV crosslinking was performed with labeled oligonucleotides corresponding to a region of the HIV-1 LTR extending from −18 to +28. HeLa nuclear extract was fractionated on a phosphocellulose column and step-eluted with KCl into 4 fractions: A (0.1M KCl eluate), B (0.3M KCl eluate), C (0.5M KCl eluate), and D (1.0M KCl eluate) (Dignam et al., 1983). About 1 μg of each of these phosphocellulose column fractions were incubated at room temperature for 10 minutes in gel-retardation buffer (50 mM KCl, 10 mM Tris pH 7.9, 0.1 mM EDTA, 10% glycerol, 0.5 mM DTT, 5 mM $MgCl_2$) with 3 μg of non-specific competitor poly (dG-dC):poly (dG-dC) in a total volume of 40 μl. $^{32}P$ end-labeled double-stranded HIV-1 LTR oligonucleotides (150,000 cpm) extending from nucleotide −18 to +28 were added to the samples and the samples incubated for an additional 20 minutes at room temperature. The samples were put on ice and irradiated with UV light for 30 min using a UV transilluminator placed about 4 cm above the samples (UVP, Inc,) (Wu et al., 1988). The 1.5 ml microcentrifuge tubes containing the samples were uncapped during the period of UV irradiation. An equal volume of SDS-PAGE sample buffer was added, the samples were heated at 95° C. for 5 minutes, and then analyzed following electrophoresis on a 10% SDS-PAGE gel by autoradiography.

Three species with molecular weights of approximately 110 kDa, 65 kDa, and 43 kDa respectively were found predominantly in the phosphocellulose A fraction. No detectable UV crosslinked species were seen using probe alone. Other UV crosslinked species were found in lesser quantities in the phosphocellulose B, C, and D fractions. These results indicated that multiple cellular factors present in HeLa nuclear extract are capable of binding to TAR DNA. The TRP-43 is in the A and B fraction.

EXAMPLE 2

Cloning of the Gene Encoding TDP-43

Since several cellular factors were demonstrated to be capable of binding to TAR DNA using UV crosslinking, the present inventors proceeded to isolate cDNAs that encoded one or more of these factors.

A random-primed λgt11 HeLa-cell spinner cDNA library, Clontech Laboratories, Palo Alto, Calif., was screened with double stranded $^{32}P$ labeled multimerized oligonucleotides corresponding to nucleotides that extend from −18 to +28 in the HIV-1 LTR (Singh et al., 1988). The sequence of one strand of these oligonucleotides used was 5'-CTGCTTTTTGCCTGTACTGGGTCTCTCT GGTTAGACCAGATCTGAG-3', SEQ ID NO:3. One million plaques from this amplified λgt11 library were screened with the labeled oligonucleotide probe and yielded six positive plaques which were confirmed by secondary and tertiary screening. Use of both wild-type and unrelated oligonucleotides corresponding to different regions in the HIV-1 LTR demonstrated that these phage encoded fusion proteins bound specifically only to the region of the HIV-1 LTR extending from −18 to +28.

The overlapping clones were identified and the longest cDNA clone (2.8 kb) contained the complete coding sequence of TDP-43 SEQ ID NO:1. Different EcoRI fragments generated from the cDNA were used in a Northern analysis with HeLa poly A selected mRNA to ensure that all the Eco R1 fragments were derived from one contiguous cDNA.

Northern blot analysis was performed using 10 μg of HeLa or 5 μg of Jurkat poly (A) selected mRNA following electrophoresis through a 1% formaldehyde/agarose gel. A human tissue Northern blot (Clontech, Palo Alto, Calif.) containing 2 μg of poly (A) selected mRNA from various human tissues was also analyzed. An EcoRI/NdeI DNA fragment of the TDP-43 cDNA corresponding to amino acids 59 to 165 was random primed labeled using a room temperature labeling kit (Pharmacia). This probe was hybridized to the Northern blots using a rapid-hybridization protocol (Amersham, Chicago, Ill.) followed by autoradiography for 4 hours.

DNA sequence analysis of six cDNAs indicated that they contained identical sequences in the portion of the cDNA between amino acids 115 and 250 different sizes though they contained cDNA inserts. The largest cDNA spans 2.8 kb and contains five EcoRI fragments each of which hybridized to the same size (2.8 kb) of poly (A) selected HeLa mRNA in Northern analysis. This result indicated that each of these cDNA fragments were derived essentially from the same cDNA (SEQ. ID No: 2). This cDNA contained in-frame stop codons in both its amino and carboxy terminus and encodes a protein of 414 amino acids that was designated as TDP-43 or TAR DNA binding protein of 43 kDa SEQ ID NO:1.

A search of GenBank indicated that a nucleic acid region encoding an amino acid sequence extending from amino acids 270 to 384 of the TDP-43 proteins corresponding cDNA had 96% nucleic acid homology with a partial cDNA of unknown function isolated from a random cDNA isolation procedure (Adams et al., 1993). Also, nucleic acid homology of 100% was noted in a 100 bp region of TDP-43 extending from amino acids 380 to 414 with a gene translocation involved in acute myelogenous leukemia (Nucifora et al., 1993).

A search of Swiss and PIR databases indicated that TDP-43 had 36% amino acid homology with a recently cloned human heterogeneous nuclear ribonucleoprotein C-like protein (Tay et al., 1992) and approximately 33% amino acid homology with both a human type A/B hnRNP protein (Khan et al., 1991) and a murine transcriptional repressor (Kameda and Miwa, 1992). In particular, the highest degree of homology TDP-43 shared with these proteins (Kameda and Miwa, 1992; Khan et al., 1991; Tay et al., 1992) was in a region of TDP-43 between amino acids 144 and 235 which was related to the previously described ribonucleoprotein (RNP) binding domains (Adam et al., 1986; Bandziulis et al., 1989; Dreyfuss et al., 1993; Kenan et al., 1991;Mattaj, 1989). TDP-43 also shared a high degree of homology in the RNP binding domain region with similar regions in the hnRNP core protein A1 and nucleoli (Bourbon et al., 1988; Buvoli et al., 1988). The RNP domain is found in a variety of RNA-binding proteins and has been demonstrated to be responsible for the RNA binding properties of these proteins. The RNP motif in these previously described proteins spans approximately 90 amino acids and contains consensus sequences designated RNP-1 and RNP-2 located about 30 amino acids apart (Bandziulis et al., 1989; Dreyfuss et al., 1993). The RNP-1 motif is an octapeptide which is the most highly conserved region within RNP-1 motif while the RNP-2 motif is a less well conserved hexapeptide sequence.

Within the RNP homology region of TDP-43, there is an unusual arrangement of the RNP-1 and RNP-2 motifs with two RNP-1 motifs, amino acids 145–152 and 227–234, respectively, flanking a single RNP-2 motif, residues 193–198. Another region of TDP-43, located between amino acids 274 and 314, is composed of a cluster of amino acids of which approximately 40 percent are glycine residues. This glycine-rich domain is similar to other glycine-rich domains which are found in a variety of RNA binding proteins and may function in nucleic acid strands separation (Ghisolfi et al., (1992) the molecular weight of this protein was 34 kD)) or in mediating protein-protein interactions (Cobianchi et al., 1988). An amino acid sequence Arg-Gly-Gly (EGG) which has been implicated in the RNA binding properties of other proteins (Kiledjian and Dreyfuss, 1992) was found by the present inventors to be present once within the glycine-rich domain of TDP-43.

Northern analysis was performed with a probe (EcoRI/NdeI DNA fragment from amino acids 59 to 165) consisting of a portion of the TDP-43 cDNA on HeLa (10 µg) and Jurkat (5 µg) poly (A) selected mRNA as well as mRNA extracted from a variety of human tissues. These human tissues were obtained from heart, brain, placenta, lung, liver, muscle, and kidney. TDP-43 hybridized to one major mRNA species of approximately 2.8 kb in both HeLa and Jurkat mRNA and also hybridized to this same sized mRNA species prepared from a variety of human tissues 2 µg mRNA/tissue. TDP-43 is constitutively expressed with some differences related primarily to the amount of RNA loaded in its level of expression among various tissues. The present inventors have also in vitro transcribed and translated TDP-43 RNA in a Promega TNT (transcription and translocation system (Madison, Wis.)) in the presence of $^{35}S$ methionine as discribed by the manufacturer Chromega (Madison, Wis.). Autoradiography revealed that TDP-43 migrated as a 43 kDa protein on SDS-PAGE consistent with its predicted molecular weight. Thus, TDP-43 is a ubiquitously expressed 43 kDa protein whose amino acid structure contains domains similar to that found in RNA binding proteins, but which does not bind to TAR RNA regions from +1 to +80 (see Example 5).

EXAMPLE 3

Endogenous TDP-43 Binds to TAR DNA in HeLa Nuclear Extract

Preparation of Polyclonal Antibodies Against TDP-43

UV crosslinking indicated that a protein of approximately 43 kDa, present in the 0.1M KCl fraction of HeLa nuclear extract eluted from a phosphocellulose column, bound specifically to TAR DNA. The present example provides results of studies carried out to determine if endogenous TDP-43 binds to TAR DNA. Western blot analysis was performed with rabbit polyclonal antisera which was raised to recombinant bacterially-produced TDP-43. (E. coli pLys S) Generation of Rabbit Polyclonal Antiserum Against TDP-43

The present application of the TDP-43 cellular protein, and portions thereof in generating antibody illustrates one particular practical utility of the protein and fragments thereof in their currently available forms.

A portion of TDP-43 corresponding to amino acids 92 to 315 OF SEQ ID NO: 1 was expressed as a gene 10 fusion protein, mixed with complete Freund's adjuvant, and injected into rabbits. Fifteen days after the first injection, another injection was given in incomplete Freund's adjuvant. Bleeding was performed 10 days after the second injection and the serum obtained was diluted 1:1 with 1.5M glycine, 3M NaCl pH 8.9. It was then loaded onto a protein A sepharose column, equilibrated with the same buffer, washed extensively with 20 column volumes, and the bound IgG was eluted with 0.1M citric acid pH 3.0 and neutralized with 1/10 volume of 3M Tris pH 8.9 at 4° C. The peak IgG fraction was dialyzed into 1XPBS at 4° C. overnight. The purified TDP-43 antisera was subsequently used in Western blot experiments.

Western Blot Analysis of Endogenous TDP-43.

Equal amounts of protein (~100 µg) from each of the phosphocellulose fractions (0.1M, 0.3M, 0.5M and 1M KCl) were subjected to electrophoresis on a 10% SDS-PAGE gel and transferred to nitrocellulose paper. The immunoreactive endogenous TDP-43 band was visualized following use of the chemoluminescence protocol (Amersham) with a 1:1,000 dilution of TDP-43 rabbit polyclonal antibody and a 1:10,000 dilution of secondary antibody.

"Shift-western" Assay of Endogenous TDP-43

The "Shift-western" assay is a modification of the published procedure (Demczuk et al., 1993). For gel retardation analysis, HeLa nuclear extract phosphocellulose fraction A (100 µg) was incubated with oligonucleotides corresponding to a region in TAR DNA between −18 and +28. The binding was performed at 30° C. for 30 minutes in buffer containing 20 mM Hepes, pH 7.9, 25 mM KCl, 2 mM spermidine, 0.1 mM EDTA, 0.5 mM DTT, bovine serum albumin at 100 µg/ml, 10% glycerol, 0.025% NP-40, 5 µg of poly (dG-dC): poly (dG-dC) and 5 mM $MgCl_2$. DNA protein complexes were subjected to electrophoresis at 4° C. with a constant voltage of 120 V. on a 5% native polyacrylamide gel containing 0.5×TBE, 1 mM EDTA, and 0.05% NP-40. Binding assays were carried out in identical triplicate sets and resolved on the same gel. After electrophoresis was completed, one set of binding assays was dried and subjected to autoradiography while the other two sets of reactions were subjected to a standard Western blot protocol as described above. The nitrocellulose blot was then divided into two halves; one half was probed with the pre-immune rabbit serum and the other half was probed with rabbit polyclonal anti-sera against TDP-43. The resultant immunoreactive TDP-43 band was then aligned with the gel-retarded DNA protein complexes seen following autoradiography.

The TDP-43 antisera detected a 43 kDa species predominantly present in the 0.1M KCl fraction with lesser amounts detected in the 0.3M KCl fraction eluted from the phosphocellulose column. The TDP-43 antibody did not detect HeLa nuclear proteins present in the 0.5M and 1.0M KCl fractions eluted from the phosphocellulose column. Pre-immune rabbit sera did not react with proteins present in any of the phosphocellulose column fractions.

The TDP-43 antibody did not result in a supershift of recombinant TDP-43 in gel retardation assays so the TDP-43 antibody was used in a "Shift-western" assay to determine whether TDP-43 present in HeLa nuclear extract bound to TAR DNA. This procedure uses gel retardation followed by Western blot analysis to determine the immunologic characteristics of different gel-retarded species (Demczuk et al., 1993). Gel retardation analysis was performed with an oligonucleotide probe extending from −18 to +28 in the HIV-1 LTR and HeLa nuclear extract eluted from a phosphocellulose column with 0.1M KCl, since endogenous TDP-43 was present predominantly in this fraction as determined by Western blot analysis. Three sets of identical gel retardation reactions were carried out. Following electrophoresis, a portion of the polyacrylamide gel containing one of the gel-retardation assays was subjected to autoradiography while the other gel portions containing the remaining two reactions were transferred to nitrocellulose paper. Western blot analysis was performed with rabbit polyclonal antibody directed against TDP-43 on one reaction and pre-immune sera on the remaining reaction. The autoradiogram and Western blots were then carefully aligned and compared. Two major gel-retarded species were seen in the autoradiogram of the gel retardation assay. One of the gel-retarded species comigrated exactly and can in fact be superimposed on the position of a species which was identified by Western blot analysis with TDP-43 antibody after gel retardation. This gel-retarded species was not detected with pre-immune sera was used in the Western blot analysis. These results indicate that endogenous TDP-43 present in HeLa nuclear extract was capable of binding to TAR DNA and that TDP-43 was a likely candidate for the 43 kDa species detected in UV crosslinking analysis with a portion of TAR DNA.

EXAMPLE 5

TDP-43 binds to TAR DNA and Does Not Bind to TAR RNA

The present example demonstrates that the TDP-43 cellular binding protein and a polypeptide thereof (AA7–414) binds specifically to a region of the HIV-1 LTR DNA extending from −18 to +28, that TDP-43 does not bind to TAR RNA, and that binding to double stranded DNA is preferred over single stranded DNA.

A portion of the TDP-43 cDNA encoding amino acids (7–414) was cloned downstream of a portion of the glutathione S-transferase protein. The fusion protein was expressed in bacteria (*E. coli* pLys S), and purified using glutathione agarose affinity chromatography (Smith and Johnson, 1988). This fusion protein was then used in gel retardation analysis with oligonucleotides corresponding to a region of the HIV-1 LTR extending from −18 to +28 in an attempt to determine the sequence motifs in TAR DNA which bound TDP-43. TDP-43 bound specifically to TAR (1 μg) DNA sequences. This binding was competed by the addition of either 5, 20 or 50-fold molar excess of unlabeled wild-type oligonucleotides, but not by a similar excess of unlabeled oligonucleotides corresponding to the adenovirus major late promoter TATA element.

Since a variety of proteins with RNP binding domains can bind nonspecifically to single stranded DNA (Cobianchi et al., 1988; Cobianchi et al., 1986; Ishikawa et al., 1993; Kolluri et al., 1991; Riva et al., 1986), the present inventors also tested whether TDP-43 was capable of binding to single stranded oligonucleotides extending from −18 to +28. There was reduced binding affinity and specificity of TDP-43 to these single stranded oligonucleotides compared to double stranded oligonucleotides.

Since the structure of TDP-43 was similar to that of other RNA binding proteins, such as hn RNPA$_1$, SnRNP, U1A, and nucleolin the present inventors also tested whether TDP-43 could bind specifically to wild-type TAR RNA. No binding to TAR RNA from +1 to +80 was detected by RNA gel retardation analysis under conditions conducive for Tat and TRP-185 binding to TAR RNA even after prolonged exposure of the gel to film. These results were consistent with the fact that the binding of TDP-43 was specific for double stranded TAR DNA.

To more carefully define the binding site for TDP-43 to sequences between −18 and +28 in the HIV-1 LTR, gel retardation was performed with recombinant TDP-43 in conjunction with competition analysis using a variety of HIV-1 LTR regulatory region oligonucleotides.

For oligonucleotide competition experiments, only the phosphocellulose column A fraction was used. The conditions were essentially the same as in Example 1 except that only 100 ng of non-specific competitor poly (dG-dC):poly (dG-dC) was used. The fraction A sample (1 μg) was incubated with 10 ng of double-stranded oligonucleotides as specific competitors at room temperature for 10 minutes prior to the addition of the $^{32}$P end-labeled probe. The sequences of the oligonucleotides used as specific competitors were: wild-type HIV-1 LTR from −18 to +28; −18 to +28 with mutations of pyrimidine-rich sequences (5'-CTGACGTACGTACGTACGTACATGCGTACGTTACGG ACCATCT-3', SEQ ID NO:4); and a region of the IL-2 promoter enhancer from −295 to −275 (5'-AATTGGAGGAAAAACTGTTTCATACAGAAGGCGT-3', SEQ ID NO:5).

Increasing amounts of 5, 20 or 50-fold molar excess of unlabeled competitor oligonucleotides extending from either −45 to +1, −45 to −13, or +10 to +50 did not significantly compete for binding of TDP-43. However, increasing amounts of unlabeled oligonucleotides extending from −18 to +28 efficiently competed for the binding of TDP-43. These results indicated that TDP-43 bound specifically to a region of the HIV-1 LTR extending from −18 to +28.

EXAMPLE 6

Determination of the Nucleotides Required for TDP-43 Binding to TAR DNA

The present example provides data demonstrating that TDP-43 binds to at least about two sets of pyrimidine-rich sequences in the HIV-1 LTR between −15 and −5 and +4 and +11.

Given the extensive region of TAR DNA that was bound by TDP-43, the nucleotide sequences bound by TDP-43 were determined using a previously described site-selection procedure (Blackwell and Weintraub, 1990; Wright et al., 1991), which reference is specifically incorporated herein by reference for this purpose. Oligonucleotides containing defined sequences on both their 5' and 3' ends and random 35-mer internal sequences were incubated with recombinant TDP-43 using gel retardation conditions. This was followed by five cycles of repeated binding, immunoprecipitation with specific TDP-43 antibody, and PCR amplification of the DNA coimmunoprecipitated with TDP-43 antibody.

Casting Procedure (Cyclic Amplification and Selection of Targets)

The target 78 mer oligonucleotide for CASTing contained specific sites for PCR amplification in addition to restriction enzyme sites flanking a central core of 35 degenerate nucleotides (Blackwell and Weintraub, 1990; Wright et al., 1991). Twenty-five μg of the single-stranded oligonucleotide was converted to double-stranded DNA by annealing a two-fold excess of the 3' primer and performing the primer extension reaction with 25 units of Taq DNA polymerase, 0.2 mM dNTPs, 1.5 mM MgCl$_2$ at 94° C. for 30 seconds, 55° C. for 1 minute, and 72° C. for 20 minutes.

To coat the magnetic beads with TDP-43 antibody, 1 ml of TDP-43 polyclonal rabbit serum was mixed with 200 μls of magnetic beads (Dynan) overnight at 4° C. The beads were collected by magnetic pull, washed with 500 λ of 1×PBS, 0.1% BSA and 0.1% NP-40, then resuspended in 200 μl of washing solution and kept at 4° C. The binding reactions were done at room temperature for 30 minutes in a total volume of 20 λ containing ⅕ of the double-stranded oligonucleotides and 100 ng of GST-TDP-43 (A.A. 7–414) protein in the same buffer as used in gel retardation analysis. Either TDP-43 coated antibody beads (5 μl) or beads coated with pre-immune sera were added, mixed gently at 4° C. for 30 minutes, the beads collected by magnetic pull, washed four times with buffer and added into a PCR reaction containing 500 pmol of both F (forward) and R (reverse) primer, 0.2 mM dNTPs, and 1.5 mM MgCl$_2$. After 10, 12, and 14 PCR cycles, 30 λ of the reaction was withdrawn and 10 λ were used to visualize the product on a 1.2% agarose gel while another 10 λ of the PCR reaction that contained the earliest detectable DNA product was used for the next round of binding and PCR selection. After 5 rounds, the DNA product from the reaction mixture was cloned directly into a pCRII vector (Invitrogen), the clones were subjected to DNA sequence analysis, and the DNA sequences from the clones were aligned and analyzed.

Twenty-one of these enriched PCR products were subjected to DNA sequencing to help determine optimal consensus binding sites for TDP-43. The common feature of these PCR products was the presence of at least eight contiguous pyrimidine residues containing alternating groups of cytidine and thymidine. A comparison of these sequences with that of TAR DNA revealed homology with two sets of pyrimidine-rich sequences in the HIV-1 LTR between −15 and −5 and +4 and +11 as shown in Table 2.

crosslinking. Wild-type and mutant oligonucleotides were $^{32}$P end-labeled and incubated with increasing amounts of recombinant full-length TDP-43 which was generated by thrombin cleavage of the GST moiety from the GST-TDP-43 fusion protein which was produced in bacteria and isolated by binding to glutathione agarose beads. The cleaved TDP-43 was approximately 95% pure and no appreciable degradation products were detected. UV crosslinking was performed with either 160 ng or 800 ng of TDP-43, wild-type oligonucleotides extending from −18 to +28 in the HIV-1 LTR generated both 43 kDa and 86 kDa UV crosslinked species whereas oligonucleotides containing mutations in either of two pyrimidine-rich sequences in TAR DNA, Δ1 or Δ2, were unable to generate either the 43 kDa or the 86 kDa species. The presence of both these UV crosslinked species suggested that TDP-43 may dimerize or two molecules of TDP-43 may simultaneously bind to the pyrimidine-rich sequences between −18 and +28 in the HIV-1 LTR.

EXAMPLE 7

UV Crosslinking of TDP-43 to TAR DNA

The present example compares the binding specificity of recombinant TDP-43 and the endogenous 43 kDa protein present in the phosphocellulose A fraction of HeLa nuclear extract detected by UV crosslinking.

UV crosslinking with cleaved, full-length recombinant TDP-43. The thrombin-cleaved recombinant TDP-43 was used in UV crosslinking experiments. The experimental conditions were essentially the same as described for UV crosslinking with HeLa nuclear extract except 1 μg of (poly dI-dC):(poly dI-dC) was used as non-specific competitor. In the experiment with unlabeled oligonucleotide as competitor, 800 ng of TDP-43 was crosslinked to labeled HIV-1 LTR oligonucleotide from −18 to +28 in the presence of either 50 fold molar excess of unlabeled −18 to +28

TABLE 2

| TAR DNA Elements Involved in the Binding of TDP-43 | |
|---|---|
| −18          −5   +4   +11         +28 | |
| WT    CTGCTTTTTGCCTGTACTGGGTCTCTCTGGTTAGACCAGATCTGAG | SEQ ID NO:6 |
| Δ1    CTGACGTACGTACGTACTGGGTCTCTCTGGTTAGACCAGATCTGAG | SEQ ID NO:7 |
| Δ2    CTGCTTTTTGCCTGTACGTACATGCGTACGTTAGACCAGATCTGAG | SEQ ID NO:8 |
| Δ1+Δ2    CTGACGTACGTACGTACGTACATGCGTACGTTAGACCAGATCTGAG | SEQ ID NO:9 |

The present inventors then determined whether mutations of either or both of these two groups of pyrimidine residues in the HIV-1 LTR designated Δ1 and Δ2 which extend between −15 and −5 and +4 and +11 respectively could eliminate the binding of TDP-43 to TAR DNA (Table 1). Gel retardation analysis indicated that TDP-43 was competed with a 5, 20 or 50-fold molar excess of unlabeled oligonucleotides extending from −18 to +28 in the HIV-1 LTR but not by these same oligonucleotides which contain mutations between −15 and −5 (Δ1), +4 and +11 (Δ2), or both of these elements (Δ1+Δ2). This indicated that mutation of either of the two pyrimidine-rich sequence motifs between −18 and +28 in the HIV-LTR, disrupted the binding of TDP-43.

To confirm these findings, oligonucleotides extending from −18 to +28 in the HIV-1 LTR or these same oligonucleotides which contain mutations in either of the two pyrimidine-rich nucleotide sequences were analyzed by UV oligonucleotide or −18 to +28 scrambled oligonucleotide (described above). In another set of experiments, both wild-type Δ1 and Δ2 oligonucleotides were annealed, labeled and UV crosslinked to 160 ng and 800 ng of TDP-43. The crosslinked products were resolved in 10% SDS-PAGE and visualized by autoradiography.

UV crosslinking using a $^{32}$P end-labeled TAR DNA probe extending from −18 to +28 to recombinant full-length TDP-43 again indicated the binding of two species of approximately 43 kDa and 86 kDa. Competition with a 50-fold molar excess of unlabeled wild-type competitor oligonucleotides eliminated both the 43 kDa and 86 kDa UV crosslinked species, while oligonucleotides mutated in the two pyrimidine sequences (Δ1+Δ2) between −18 and +28 did not compete for the binding of either of these species.

The present inventors determined whether the binding specificity of the 43 kDa species detected in HeLa nuclear extract by UV crosslinking was similar to that of recombinant TDP-43. UV crosslinking was performed with the phosphocellulose A fraction of HeLa nuclear extract and a labeled oligonucleotide probe extending from −18 to +28 in the HIV-1 LTR. Wild-type oligonucleotides competed for each of the three UV crosslinked species in the HIV-1 LTR phosphocellulose A fraction while these same oligonucleotides containing mutations of both the pyrimidine-rich sequences or unrelated oligonucleotides corresponding to either the adenovirus major late promoter TATA element or IL-2 promoter sequences, corresponding to residues −295 to −275 did not compete for the binding of the 43 kDa UV crosslinked species. These results indicated that a protein species of approximately 43 kDa present in the phosphocellulose column A fraction of HeLa nuclear extract possesses similar DNA binding activity in UV crosslinking assays as the recombinant full-length TDP-43 protein.

EXAMPLE 8

RNP Motifs of TDP-43 are Important for DNA Binding

The present example provides results of studies carried out by the present inventors to determine which domains in the TDP-43 protein are responsible for its binding to the HIV-1 LTR. In particular, the present inventors investigated whether either the glycine-rich domain which contains an RGG motif or the RNP domains were critical for TDP-43 binding to DNA.

Construction of TDP-43 carboxy-terminal truncation mutants. TDP-43 (amino acid 7–414) was cloned downstream of glutathione S-transferase (62) using a three-way ligation with a BstEII (end-filled)/BamHI cut TDP-43 cDNA fragment, a 967 bp BamHI/PstI from pGEX-2T and a 3986 bp SmaI/PstI cut pGEX-2T fragment so as the resultant vector had duplicated BamHI and Sma I sites in front of the BamHI site in the polylinker of pGEX-2T. Carboxy-terminal truncations of TDP-43 fused to GST were also constructed. TDP-43 (amino acids 7–333) was generated in a three-way ligation using a BamHI/NcoI fragment from TDP-43 (amino acid 7–414) clone and an NcoI/EcoR1 fragment from TDP-43 cDNA cloned into a BamHI/EcoRI cut pGEX-2T vector. A GST TDP-43 (amino acid 7–240) construct was generated by cloning a BamHI/FspI fragment from the TDP-43 (amino acids 7–414) clone into a BamHI/SmaI cut pGEX-2T vector. A GST TDP-43 (amino acids 7–198) construct was generated in a three-way ligation using a BamHI/NdeI fragment. The TDP-43 (amino acids 7–166) construct was generated by ligating a Bam HI/NdeI (end-filled) fragment from TDP-43 (amino acids 7–414) clone into a Bam HI/SmaI cut pGEX-2T vector. Finally, a GST TDP-43 (amino acid 7–125) construct was generated by cloning a NdeI/RsaI fragment from this vector with a BamHI/Rsa I fragment from TDP-43 (amino acids 7–414) into a BamHI/Sma I cut pGEX-2T vector. All the TDP-43 fusion proteins with glutathione S-transferase were purified as described (Smith and Johnson, 1988) by manufacturer (Pharmacia) and visualized on a 10% SDS-PAGE gel by Coomassie blue staining.

Gel retardation analysis with wild-type and truncated TDP-43 proteins. The wild-type and truncated TDP-43 cDNAs expressed as GST fusion proteins were purified and used in gel retardation analysis with a $^{32}P$ end-labeled, double-stranded oligonucleotide corresponding to −18 to +28 in the HIV-1 LTR. Either 1 µg of GST-TDP-43 or GST protein were incubated at room temperature for 10 minutes in gel-retardation buffer containing 50 mM KCl, 10 mM Tris pH 7.9, 5 mM MgCl$_2$, 10% glycerol, 0.1 mM EDTA, 0.5 mM DTT and 1 µg of poly (dI-dC): poly (dI-dC). For competition 10, 20 and 50 ng of unlabeled double-stranded oligonucleotides were added either as specific or non-specific competitors followed by the addition of 100,000 cpm of labeled probe incubated at room temperature for 20 minutes. The resultant protein-DNA complex was resolved by electrophoresis at 120V on a 6% native polyacrylamide gel containing ½×TBE at 4° C. followed by autoradiography. For gel-retardation analysis with wild-type TDP-43, oligonucleotide competitors included those from the adenovirus major late promoter (AdMLP) and the HIV-1 LTR indicated by nucleotides are shown below:

AdMLP TATA 5'-AAGGGGGGCTATAAAAGG
GGGTGGGGG-3',  SEQ ID NO:10

−45/+1 5'-GCGTGCCTCAGATGCTGCATATAAGCAG-
CAGCTGCTTTTTGCCTGTACT-3',  SEQ ID NO:11

−46/−13 5'-GCGTGCCTCAGATGCTGCATATAAG-
CAGCTGCTTT-3',  SEQ ID NO:12

+10/+50 5'-GGTTAGACCAGATCTGAGCCTGG-
GAGCTCTCTGGCTAACTAG-3', SEQ ID NO: 13

In another set of experiments, a region of the HIV-1 LTR extending from −18 to +28 which contained either wild-type (WT) or mutated sequences in two pyrimidine-rich sequences (Δ1, Δ2, Δ1 and Δ2) as shown:

WT 5'-CTGCTTTTTGCCTG-
TACTGGGTCTCTCTGGTTAGACCAG
ATCT-3',  SEQ ID NO:14

Δ1 5'-CTG<u>ACGT</u><u>ACGT</u><u>ACG</u>TACTGGGTCTCTCTGGTTAGAC
CAGATCT-3',  SEQ ID NO:15

Δ2 5'-CTGCTTTTTGCCTGTAC<u>GTACATG</u>C
<u>GTAC</u>GTTAGACCAGATCT-3',  SEQ ID NO:16

Δ1+Δ2 5'-CTG<u>ACGT</u><u>ACG</u><u>TAC</u>GTAC<u>GTACATG</u>C
<u>GTAC</u>GTTACGGACCATCT-3',  SEQ ID NO:17

The carboxyl-terminal truncations of the TDP-43 protein fused to glutathione S-transferase were produced in bacteria (E. coli ply S S) and purified using glutathione agarose affinity beads. A schematic of their structure is shown in FIG. 1. These fusion proteins that contained progressively deleted portions of TDP-43 including the glycine-rich domain, RNP-1 (Adams et al., 1993), RNP-2, and RNP-1 (Adam et al., 1986), were used in gel retardation analysis with a labeled oligonucleotide probe extending from −18 to +28 in the HIV-1 LTR. Truncations which deleted the glycine-rich domain bound like wild-type TDP-43. Truncations which deleted most of the RNP binding domain including RNP-1 (Adams et al., 1993) and RNP-2 also bound to the oligonucleotide probe. However, deletion of RNP-1 that removed the entire RNP binding motif, and the entire glycine-rich domain eliminated the ability of TDP-43 to bind to TAR DNA. The RNP binding motif is defined as including both the RNP1 and RNP2 regions. These results established that deletion of RNP-1 that removes the entire RNP binding motif will eliminate the DNA binding properties of TDP-43. These results also demonstrate that the presence of only part of the RNP binding motif will retain DNA binding properties of the TDP-43, or a polypeptide fragment thereof. It appears that DNA binding is retained with only the RNP1 region of the motif. Binding affinity was observed to be higher in the presence of both RNP1 and RNP2.

EXAMPLE 9

TDP-43 Represses Basal and Tat-Induced HIV Gene Expression

The present example provides data from studies carried out to determine the role of TDP-43 on HIV-1 gene expression in both the presence and absence of the transactivator protein, Tat. To directly assay the effect of the recombinant TDP-43 protein, in vitro transcription assays were performed.

A thrombin-cleaved, full length TDP-43 protein generated from GST-TDP-43 as described in Example 1, was added to in vitro transcription assays with a linearized HIV-1 LTR template and HeLa nuclear extract in both the absence and presence of bacterial produced Tat (Kato et al., 1991; Marciniak et al., 1990). The amount of TDP-43 protein added to the in vitro transcription assays was that used in UV crosslinking experiments of TDP-43 to the HIV-1 LTR in Examples 6 and 7. The HIV-1 LTR when linearized with SpeI generated an 1100 bp run-off product which was inhibited by α amanitin.

Generation of a full-length recombinant TDP-43. To generate a full-length recombinant TDP-43, an NcoI site was engineered at the beginning of TDP-43 cDNA as the initiating methionine by PCR. The PCR product was then sequenced and cloned as a partial NcoI/XhoI fragment into pGEX-KG. Full-length cleaved TDP-43 was then produced by thrombin cleavage as described (Wu et al., 1991). This thrombin-cleaved, bacterially produced full-length TDP-43 was used in UV cross-linking and in vitro transcription experiments.

In vitro transcription assays with TDP-43. The HIV-1 template is a 5' proviral construct cloned into pUC19 and was linearized at the SpeI restriction site in the gag gene. The SpeI linearized template gives a run-off transcript of about 1100 bp. Transcription reactions were carried out in a 25–50 μl with a final concentration of 10 mM HEPES (pH 7.9), 50 mM KCl, 0.25 mM DTT, 3 mM MgCl$_2$, 10% glycerol, 0.1 mM EDTA, 40 u of RNasin (Promega), 0.4 mM each of ATP, CTP, and UTP, 16 μM of GTP, 10 μCi of $^{32}$P-αGTP (added at 30 minutes into the reaction) and 200 ng of linearized template at 30° C. for 1 hr. HeLa nuclear extract was purchased from Promega and used according to manufacturer's specification. Tat protein used in the transcription reaction was cleaved and purified from GST-Tat with a modified procedure as described (Wu et al., 1991) and shown to be active in vitro transcription with the HIV-1 LTR. After the completion of reactions, the transcription was stopped by addition of 450 μl of stop solution containing 7.0M urea, 0.1M Tris HCl (pH 7.4), 0.5M NaCl, 0.5% SDS and 10 mM EDTA. The transcription product was extracted with phenol-chloroform, precipitated with 1 μg of oyster glycogen and ethanol, and resolved on a 5% denaturing polyacrylamide gel (7M urea, 1×TBE) electrophoresis at 60 W.

In the first set of reactions, the linearized HIV template was incubated at room temperature for 20 minutes in the presence or absence of 800 ng of purified TDP-43. After the addition of HeLa nuclear extract and Tat, the reactions were incubated at 30° C. for 30 min, $^{32}$P-αGTP was then added and the reaction continued for another 30 min at 30° C. In the second set of reactions, 800 ng of TDP-43 was added either 20 minutes prior to the addition of HeLa nuclear extract and Tat, simultaneously with nuclear extract and Tat or added 30 minutes after addition of HeLa nuclear extract and Tat. In all reactions $^{32}$P-αGTP was added 30 minutes after addition of HeLa nuclear extract and Tat. In the third set of reactions, a linearized adenovirus major late promoter template was used as an internal control. Either 0, 160 ng or 800 ng of TDP-43 was incubated with the HIV-1 and adenovirus major late promoter templates at room temperature for 20 minutes prior to the addition of HeLa nuclear extract. The reactions were then incubated at 30° C., for 30 minutes, $^{32}$P-αGTP was added, and the reactions were continued at 30° C. for 30 minutes before termination.

Tat strongly activated gene expression from the HIV-1 LTR using previously described assay conditions (Marciniak et al., 1990). However, when TDP-43 was pre-incubated with the HIV-1 LTR template 20 minutes prior to the addition of Tat and nuclear extract, a marked inhibition of both basal and Tat-induced gene expression was noted.

Experiments were then performed to determine the mechanism by which TDP-43 repressed in vitro transcription from the HIV-1 LTR. In these experiments, the $^{32}$P labeled ribonucleotide, $^{32}$P-αGTP, was added 30 min after the addition of Tat and HeLa nuclear extract and the reaction was stopped 30 minutes later so that each reaction contained the labeled ribonucleotide for the same amount of time. Similar to the results of the first set of reactions, TDP-43 added 20 minutes prior to the addition of Tat resulted in little activation by Tat. When TDP-43 was added simultaneously with Tat and nuclear extract, there was a moderate increase in Tat transactivation. Finally, when TDP-43 was added 30 min after the addition of Tat and nuclear extract, there was a much larger increase in Tat activation. To demonstrate that the effects of TDP-43 were specific for the HIV-1 promoter, increasing amounts of TDP-43 were incubated in in vitro transcription assays with both HIV-1 and adenovirus major late template. Increasing the amount of TDP-43 progressively decreased the basal level of transcription from the HIV-1 LTR but not from the adenovirus major late promoter. These results were consistent with a model in which the binding of TDP-43 to the HIV-1 LTR prevented the assembly of transcription complexes which were targets for subsequent Tat-activation.

The in vitro transcription results with TDP-43 indicated that pre-incubation of TDP-43 with the HIV-1 template is necessary for maximal repression of both basal and Tat-induced gene expression. Simultaneous addition of nuclear extract and TDP-43 resulted in less repression of basal and Tat-induced transcription. Addition of TDP-43 after the addition HeLa nuclear extract resulted in very minimal amounts of repression of basal and Tat-induced gene expression. These observations, suggest that the mechanism of transcriptional repression of HIV-1 gene expression by TDP-43 may be explained by its ability to block the assembly of a transcriptional initiation complex which is competent to respond to Tat.

EXAMPLE 10

Monoclonal Antibodies to TDP-43

Monoclonal antibodies raised against TDP-43 are obtained as described in this example. These antibodies are useful for (1) screening a cDNA expression library in the process of cloning the gene that encodes TDP-43 (for example, the SUPERSCREEN® immunoscreening system from AMERSHAM®), facilitating the purification of TDP-43 by using column chromatography to which the monoclonal antibody is bound, and (3) providing reagents necessary for a diagnostic immunoassay for screening biological samples.

Monoclonal antibodies are obtained using the following procedure, (Harlow, E. and D. Lane., 1988).

Immunization Schedule for Raising Monoclonal Antibodies
1. For each mouse, mix 250 μl of antigen solution containing 10 μg of TDP-43 with 250 μl of complete Freund's adjuvant. Inject six BALB/c female mice ip (intraperitoneal injection).
2. After 14 days, repeat the injections of TDP-43 and incomplete Freund's adjuvant.

3. Collect tail bleeds from immunized mice on day 24. Do 1 in 5 dilutions in phosphate buffered saline (PBS) and test all samples by comparison with similar dilutions of normal mouse serum in a dot blot.

4. On day 35, inject all animals ip with TDP-43 and incomplete Freund's.

5. Day 45, do tail bleeds and test by dot blot. All serum samples checked by immunoprecipitation against in vivo radiolabeled antigen preparation.

6. Day 56, inject best responder, 100 µl iv and 100 µl ip. All others get ip injection with incomplete Freund's.

7. Day 59, fuse splenocytes from best responder.

The resultant hybridoma tissue culture supernatants are screened for monoclonal antibodies as follows:

1. A protein solution of at least 1 µg/ml of TDP-43 is added to a nitrocellulose sheet at 0.1 ml/cm$^2$. Allow the protein to bind to the paper for 1 hr. Higher concentrations of proteins will increase the signal and make screening faster and easier. If the amount of protein is not limiting, concentrations of 10–50 µg/ml should be used. Nitrocellulose can bind approximately 100 µg of protein per cm$^2$.

2. Wash the nitrocellulose sheet three times in PBS.

3. Place the sheet in a solution of 3% BSA in PBS with 0.02% sodium azide for 2 hr to overnight. To store the sheet, wash twice in PBS and place at 4° C. with 0.02% sodium azide. For long-term storage, shake off excessive moisture from the sheet, cover in plastic wrap, and store at −70° C.

4. Place the wet sheet on a piece of parafilm, and rule with a soft lead pencil in 3-mm squares. Cut off enough paper for the number of assays.

5. Apply 1 µl of the hybridoma tissue culture supernatant to each square. Incubate the nitrocellulose sheet on the parafilm at room temperature in a humid atmosphere for 30 min.

Along with dilutions of normal mouse serum, include dilutions of the mouse serum from the last test bleed as controls. Dilutions of the test sera are essential to control correctly for the strength of the positive signals. Mouse sera will often contain numerous antibodies to different regions of the antigen and therefore will give a stronger signal than a monoclonal antibody. Therefore, dilutions need to be used to lower the signal. Good monoclonal antibodies will appear 10-fold less potent than good polyclonal sera.

6. Quickly wash the sheet three times with PBS, then wash two times for 5 min each with PBS.

7. Add 50,000 cpm of $^{125}$I-labeled rabbit anti-mouse immunoglobulin per 3-mm square in 3% BSA/PBS with 0.02% sodium azide (about 2.0 ml/cm$^2$).

8. After 30–60 min of incubation with shaking at room temperature, wash extensively with PBS until counts in the wash buffer approach background levels.

9. Cover in plastic wrap and expose to X-ray film with a screen at −70° C.

The hybridoma identified as producing antibody to TDP-43 is passaged as follows:

1. Inject 10$^7$ (or less) cells into female mice that have been injected ip about 1 week earlier with 0.5 ml of pristane or incomplete Freund's adjuvant. These types of injections are also used to prime mice for ascites production, and this may serve as a convenient source of appropriate hosts. If no mice are available, inject mice with incomplete Freund's adjuvant and wait 4 hr to 1 day before injecting the hybridoma cells. The animals must be of the same genetic background as your cell line.

2. If an ascites develops, tap the fluid and transfer into a sterile centrifuge tube.

3. Spin the ascites at 400 g for 5 min at room temperature.

4. Remove the supernatant. Resuspend the cell pellet in 10 ml of medium supplemented with 10% fetal bovine serum and transfer to a tissue culture plate. The supernatant can be checked for the presence of the antibody and used for further work if needed.

5. Handle as for normal hybridomas, except keep the cells separate from the other cultures until there is little chance of the contamination reappearing.

EXAMPLE 11

Proposed Method for Preparing a Therapeutic Agent for the Treatment of AIDS

The present prophetic example is provided to outline a method which may be used to treat patients infected with the HIV or HTLV virus. The TDP-43 cellular protein is demonstrated to repress HIV gene expression by binding a particular TAR region of the HIV DNA LTR. Therefore, it is contemplated that preparations that include either the recombinant or all extracted forms of the TDP-43 protein, or vectors or plasmids containing the nucleic acid sequence for this protein, will be useful for inhibiting the HIV virus, and thus effect a treatment for the disease.

EXAMPLE 12

Immunodiagnostic Assay for HIV Infection

This prophetic example outlines a method which may be useful for the diagnosis and clinical monitoring of the progression of an HIV infection, such as AIDS, in a human. The method employs the monitoring of the levels of, for example, antibodies specific for the TDP-43 cellular protein.

EXAMPLE 13

Gene Therapy

This prophetic example describes some of the ways in which the present invention may be of use in the treatment of AIDS, AIDS related complex and related retroviral infections via gene therapy. A TDP-43 gene, or fragment thereof, may be introduced into human tissue to provide the TDP-43 protein product, or fragment thereof, that would bind the −18 to +28 region of TAR DNA of the HIV-1 LTR and would repress expression and, therefore, would repress activation of the virus. Although it appears that TDP-43 does not remove Tat once Tat is bound to TAR, it is the case that upon multiple rounds of replication in the presence of TDP-43 that TDP-43 would bind to TAR and effectively compete out Tat.

Human adenoviruses or retrovirus are means for introducing genes into tissue. Adenoviruses are double-stranded DNA tumor viruses with genome sizes of approximate 36 kb. As a model system for eukaryotic gene expression, adenoviruses have been widely studied and well characterized, which makes them an attractive system for development of adenovirus as a gene retroviral vector-paper transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers. Persistent expression of transgenes follows adenoviral infection.

Particular advantages of an adenovirus system for delivering foreign genes and their protein products to a cell include (i) the ability to substitute relatively large pieces of vital DNA with foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Human subjects testing positive for HIV or related viral infection and for whom the medical indication for adenovirus-mediated gene transfer has been established would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus providing the TDP-43 gene is prepared and purified by any method that would be acceptable to the Food and Drug Administration for administration to human subjects, including, but not limited to cesium chloride density gradient centrifugation, and subsequently tested for efficacy and purity. Virus is administered to patients by means of intravenous administration in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

Patients would remain hospitalized for at least 48 hr to monitor acute and delayed adverse reactions. Serum levels of a protein product may be monitored or Southern blots may be performed to follow the efficacy of the gene transfer. Adjustments to the treatment may include adenovirus constructs that use different promoters or a change in the number of pfu injected.

EXAMPLE 14

TDP-43

Markedly Inhibits the Expression of HIV

The present example is provided to demonstrate the utility of using the sequences encoding the TDP-43 cellular binding protein or polypeptide fragments thereof having the defined characteristics, for inhibiting HIV infection, such as in AIDS, ARC and other HIV related pathologies. The present example also illustrates the utility of the TDP-43, and polypeptide fragments thereof, for inhibiting the expression of HIV in HIV-infected human cells, such as in HeLa cells.

Surprisingly, the data of the present study demonstrates a tremendous decrease of 15 to 20-fold in p24 expression by HeLa cells transfected with an infectious HIV-proviral clone when co-transfected with TDP-43, at the 3 day time period examined. Even at 6 days post-transfection, there was an observable 4-fold decrease in the amount of p24 with TDP-43 as compared to the control. In addition, a construct which deleted all of the RNP binding motifs allowed nearly wild type levels of HIV-1 gene expression.

The present results demonstrate that TDP-43 is a potent inhibitor of HIV-1 gene expression using in vitro and the in vivo expression assays.

Analysis of TDP-43 Effects on HIV-1 Gene Expression

HeLa cells were maintained in complete Iscove's media supplemented with 5% newborn calf serum, 2.5% fetal bovine serum, and 1% penicillin and streptomycin. One day before transfection, 60 mm plates were seeded with $3 \times 10^5$ HeLa cells so that the plates were 50–70% cofluent at the time of transfection. The lipofectamine transfection method (BRL) was used to co-transfect 1 µg of a wild type HIV-1 proviral construct (Harrich et al. (1990) EMBOJ, 9:4417–23)) with 1 µg of an RSV-β-galactosidase expression vector to monitor transfection efficiencies. All transfections were performed three times. On day 3 and 6, 0.5 mls of culture supernatants were removed from each transfection and assayed for p24 antigen using the Abbott HIV AG ELISA system (Id.). The cells were fixed, stained for β-galactosidase activity, and the total number of positive cells was determined for each transfection. The p24 antigen levels were normalized to reflect the transfection efficiency.

TDP-43 Represses HIV-1 Gene Expression In Vivo

Figure 2:
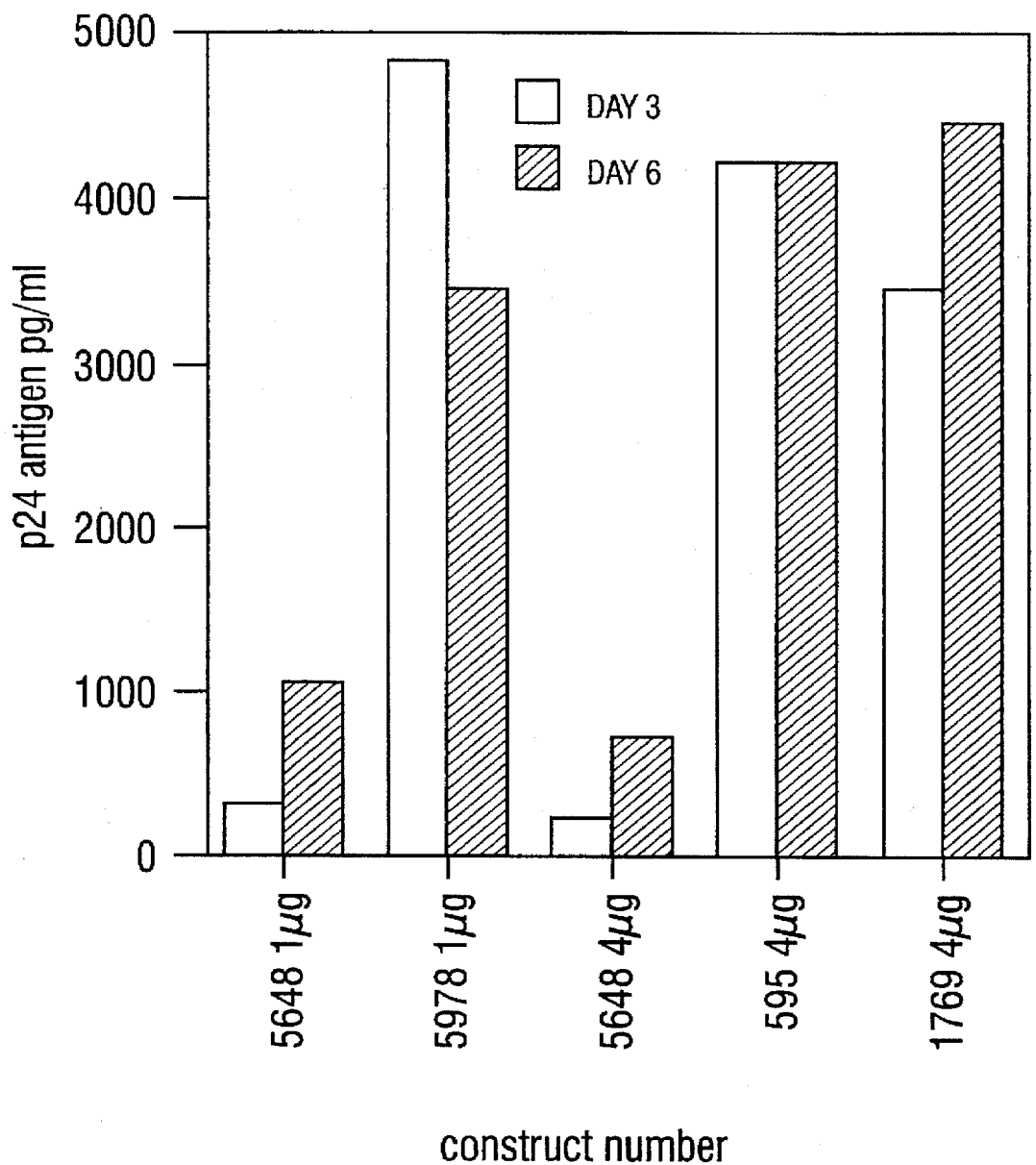
FIG. 2 shows that TDP-43 represses HIV-1 proviral gene expression in vivo.

To determine if TDP-43 could repress HIV-1 gene expression in vivo, TDP-43 was inserted downstream of the TSV promoter in a eucaryotic expression vector. As controls, either a construct that deleted the RNP binding motifs in TDP-43, (RSV-ΔTDP-43) or sequences encoding the first exon of the rabbit β-globin gene were cloned into the same vector. HeLa cells were transfected with 1 µg of an HIV-1 proviral molecular isolate which has been demonstrated to express high level of HIV-1 gene expression following transfection (Harrich et al. (1990)). Each transfection included RSV-β-galactosidase to control for variations in transfection efficiencies. Three and six days post-transfection culture supernatant was removed from each transfection and assayed by ELISA for soluble HIV-1 p24 antigen. After three days, RSV-TDP-43 repressed HIV-1 gene expression 16 to 20-fold compared to transfections with RSV-ΔTDP-43, RSV-β-globin, or the RSV-vector respectively (FIG. 2). By day six, RSV-TDP-43 inhibited HIV-1 gene approximately four-fold compared to TSV-ΔTDP-43, RSV-β-globin, or the TSV-vector respectively (FIG. 2). The β-galactosidase activity indicated that the efficiencies of all transfections were nearly identical. Furthermore the transfection of RSV expression vectors encoding a variety of other transcription factors including ILF, which binds to the HIV-1 negative regulatory element, or unrelated transcription factors such as CREB, had no effects on expression from the HIV-1 provirus. These results indicate that TDP-43 is a potent inhibitor of HIV-1 gene expression.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adam, S. A. et al., *Mol. Cell. Biol.* 6:2932–2943, 1986.
Adams, M. D. et al., *Nature Genet.* 4:373–380, 1993.
Bandziulis, R. J. et al., *Genes & Dev.* 3:431–437, 1989.
Berkhout, B. and K.-T. Jeang, *J. Virol.* 66:139–149, 1992.
Berkhout, B. et al., *Cell* 62:757–767, 1990.
Barkhout, B. et al., *Cell* 59:273–282, 1989.
Blackwell, T. K. and H. Weintraub, *Science* 250:1104–1110, 1990.
Bourbon, H. M. et al., *J. Mol. Biol.* 200:627–638, 1988.
Buvoli M. et al., *Nucl. Acids. Res.* 16:3751–3770, 1988.
Calnan, B. J. et al., *Science* 252:1167–1171, 1991.
Calnan, B. J. et al., *Genes & Dev.* 5:201–210, 1991.
Cobianchi, F. et al., *J. Biol. Chem.* 263:1063–1071, 1988.
Cobianchi, F. et al., *J. Biol. Chem.* 261:3536–3543, 1986.
Demczuk, S. et al., *Proc. Natl. Acad. Sci. USA* 90:2574–2578, 1993.
Dignam, J. D., et al., *Nucl. Acids Res.* 11:1475–1489, 1983.
Dingwall, C. et al., *EMBO J.* 9:4145–4153, 1990.
Dreyfuss, G. et al., *Annu. Rev. Biochem.* 62:289–321, 1993.
Du, H. et al., *EMBO* 12:501–511, 1993.
Feinberg, M. B. et al., *Proc. Natl. Acad. Sci. USA* 88:4045–4049, 1991.
Feng, S. and E. C. Holland, *Nature* 334:165–167, 1988.
Garcia, J. A. et al., *EMBO J.* 8:765–778, 1989.
Garcia, J. A. et al., *EMBO* 6:3761–3770, 1987.
Gaynor, R., *AIDS* 6:347–363, 1992.
Ghisolfi, L. et al., *J. Biol. Chem.* 267:2944–2959, 1992.
Harrich, D. et al., *EMBO J.* 9:4417–4423, 1990.
Hauber, J. and B. R. Cullen, *J. Virol.* 62:673–679, 1988.
Howell, E. and D. Lane, *Antibodies, "A Laboratory Manual"*, Cold Spring Harbor Laboratory, Cold Spring Harbor, N.Y., 1988.
Ishikawa, F. et al., *Mol. Cell. Biol.* 13:4301–4310, 1993.
Jones, K. A. et al., *Genes & Dev.* 2:1101–1114, 1988.
Jones, K. A. et al., *Science* 232:755–759, 1986.
Kameda, S. and T. Miwa, *Gene* 119:229–236, 1992.
Kao, S.-Y. et al., *Nature* 330:489–493, 1987.
Kato, H. et al., *Genes & Dev.* 6:655–666, 1992.
Kato, H. et al., *Science* 251:1476–1479, 1991.
Kenan, D. J. et al., *TIBS* 16:214–220, 1991.
Khan, F. A. et al., *FEBS Letter* 290:159–161, 1991.
Kiledjian, M. and G. Dreyfuss, *EMBO J.* 11:2655–2664, 1992.
Kolluri, R. et al., *NAR* 20:111–116, 1992.
Kolluri, R. and A. J. Kinniburgh, *Nucl. Acids Research* 19:4771, 1991.
Laspia, M. et al., *Cell* 59:283–292, 1989.
Lehnherr et al., *J. Bacteriol* 174:6138–6144, 1992.
Lu, X. et al., *J. Virol.* 67:1752–1760, 1993.
Malim, M. H. et al., *J. Virol.* 63:3213–9, 1989.
Marciniak, R. A. and P. A. Sharp, *EMBO J.* 10:4189–4196, 1991.
Marciniak, R. A. et al., *Cell* 63:791–802, 1990.
Matsui, T. et al., *J. Biol. Chem.* 255:11992–11996, 1980.
Mattaj, I. W., *Cell* 57:1–3, 1989.
Meisterernst, M. and R. Roeder, *Cell* 67:557–567, 1991.
Morgenstern et al. (1990), Nucleic Acids Research, 18(12):3587–96
Nabel, G. and D. Baltimore, *Nature* 326:711–713, 1987.
Nucifora, G. et al., *Blood* 81:2728–2734, 1993.
Olsen, H. S. and C. A. Rosen, *J. Virol.* 66:5594–5597, 1992.
Ratnasabapathy, R. et al., *Genes & Dev.* 4:2061–2074, 1990.
Riva, S. et al., *EMBO J.* 5:2267–2273, 1986.
Rosen, C. A. et al., *Cell* 41:813–823, 1985.
Roy, A. L. et al., *Nature* 354:245–248, 1991.
Roy, S. et al., *Science* 247:1216–1219, 1990.
Sambrook, et al., *Molecular Cloning: A Laboratory Manual*. Cold Spring Harbor Laboratory, Cold Spring Harbor, N.Y., 1989.
Selby, M. J. and B. M. Peterlin, *Cell* 62:769–776, 1990.
Sheldon, M. et al., *MCB* 13:125 1–1263, 1993.
Sheline, C. T. et al., *Genes Dev.* 5:2508–2520, 1991.
Singh, H. et al., *Cell* 52:415–423, 1988.
Smith, D. B. and K. S. Johnson, *Gene* 67:31–40, 1988.
Staudt, L. M. et al., *Nature* 323:640–643, 1986.
Tay, N. et al., *J. Virol.* 66:6841–6848, 1992.
Verdin, E. et al., *EMBO J.* 12:3249–3599, 1993.
Weeks, K. M. and D. M. Crothers, *Cell* 66:577–588, 1991.
Wright, E. E. et al., *Mol. Cell Biol.* 11:4104–4110, 1991.
Wu, F. et al., *Genes & Dev.* 5:2128–2140, 1991.
Wu, F. K. et al., *EMBO J.* 7:2117–2129, 1988.
Yoshimura, T. et al., *EMBO J.* 9:2537–2542, 1990.
Zenzie-Gregory, B. and S. T. Smale, *J. Biol. Chem.* 268:15823–15832, 1993.

---

What is claimed is:

1. A polypeptide that binds a TAR region of HIV-1 LTR DNA, does not bind to TAR RNA, and that inhibits HIV-1 gene expression, wherein said polypeptide is further defined as comprising a sequence 7–125 of SEQ ID NO:1.

2. The polypeptide of claim 1 further defined as TDP-43.

3. The polypeptide of claim 1 comprising an RNP-1 region of an RNP binding motif.

4. The polypeptide of claim 1 defined as being about 118 to about 1,000 amino acids in length.

5. The polypeptide of claim 4 further defined as being about 150 to about 450 amino acids in length.

6. The polypeptide of claim 1 having a molecular weight of about 40 kD to about 46 kD as determined by SDS polyacrylamide gel electrophoresis.

7. The polypeptide of claim 6 further defined as having a molecular weight of about 43 kD as determined by SDS polyacrylamide gel electrophoresis.

8. A polypeptide that binds to a TAR region of HIV LTR DNA, that does not bind to TAR RNA, and that inhibits HIV-1 gene expression, prepared by a process comprising the steps of:

preparing a nuclear extract of animal cells;
   fractionating the nuclear extract;
   collecting fractions containing a polypeptide that binds a TAR region of HIV LTR DNA, that does not bind to TAR RNA and that inhibits HIV-1 gene expression.

9. The polypeptide of claim 8 further defined as comprising a sequence 92–125 of SEQ ID NO:1.

10. The polypeptide of claim 8 further defined as a cellular binding protein having a molecular weight of between about 40 kD and about 46 kD as determined by SDS polyacrylamide gel electrophoresis.

11. The polypeptide of claim 8 where the cellular binding protein is further defined as having a molecular weight of about 43 kD as determined by SDS polyacrylamide gel electrophoresis.

12. A pharmaceutical preparation comprising the polypeptide of claim 1 in a pharmaceutically acceptable carrier.

13. A method for inhibiting HIV-1 gene expression comprising administering to cells infected with human immunodeficiency virus a preparation comprising a polypeptide having an amino acid sequence 7–125 of SEQ ID NO:1.

14. The method of claim 13 where the polypeptide has a molecular weight of about 40 kD to about 46 kD as determined by SDS polyacrylamide gel electrophoresis.

15. A polypeptide that binds a TAR region of HIV-1 LTR DNA, does not bind to TAR RNA, and that inhibits HIV-1 gene expression.

16. The polypeptide of claim 15, comprising an amino acid sequence selected from the group consisting of 7–166, 7–198, 7–240, 7–333, 7–414, 7–421 and 92–315 of SEQ ID NO:1.

17. The polypeptide of claim 15, encoded by a nucleic acid comprising a nucleotide sequence selected from the group consisting of a 21–375, 21–498, 21–594, 21–720, 21–999, 21–1263 and 276–375 of SEQ ID NO:2.

18. The polypeptide of claim 15, further defined as a fusion protein.

19. The polypeptide of claim 18, wherein said fusion protein is further defined as a comprising a glutathione S-transferase protein and said polypeptide.

20. The polypeptide of claim 18, wherein said fusion protein is further defined as comprising a gene 10 protein and said polypeptide.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 414 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

Met Ser Glu Tyr Ile Arg Val Thr Glu Asp Glu Asn Asp Glu Pro Ile

|   | 1 | 5 | 10 | 15 |
|---|---|---|---|---|

Glu Ile Pro Ser Glu Asp Asp Gly Thr Val Leu Leu Ser Thr Val Thr
                20                    25                30

Ala Gln Phe Pro Gly Ala Cys Gly Leu Arg Tyr Arg Asn Pro Val Ser
            35              40                45

Gln Cys Met Arg Gly Val Arg Leu Val Glu Gly Ile Leu His Ala Pro
        50              55                60

Asp Ala Gly Trp Gly Asn Leu Val Tyr Val Asn Tyr Pro Lys Asp
65                      70                75                      80

Asn Lys Arg Lys Met Asp Glu Thr Asp Ala Ser Ser Ala Val Lys Val
                85                  90                  95

Lys Arg Ala Val Gln Lys Thr Ser Asp Leu Ile Val Leu Gly Leu Pro
            100             105             110

Trp Lys Thr Thr Glu Gln Asp Leu Lys Glu Tyr Phe Ser Thr Phe Gly
        115             120             125

Glu Val Leu Met Val Gln Val Lys Lys Asp Leu Lys Thr Gly His Ser
    130             135             140

Lys Gly Phe Gly Phe Val Arg Phe Thr Glu Tyr Glu Thr Gln Val Lys
145             150             155             160

Val Met Ser Gln Arg His Met Ile Asp Gly Arg Trp Cys Asp Cys Lys
            165             170             175

Leu Pro Asn Ser Lys Gln Ser Gln Asp Glu Pro Leu Arg Ser Arg Lys
            180             185             190

Val Phe Val Gly Arg Cys Thr Glu Asp Met Thr Glu Asp Glu Leu Arg
        195             200             205

Glu Phe Phe Ser Gln Tyr Gly Asp Val Met Asp Val Phe Ile Pro Lys
    210             215             220

Pro Phe Arg Ala Phe Ala Phe Val Thr Phe Ala Asp Asp Gln Ile Ala
225             230             235             240

Gln Ser Leu Cys Gly Glu Asp Leu Ile Ile Lys Gly Ile Ser Val His
            245             250             255

Ile Ser Asn Ala Glu Pro Lys His Asn Ser Asn Arg Gln Leu Glu Arg
            260             265             270

Ser Gly Arg Phe Gly Gly Asn Pro Gly Gly Phe Gly Asn Gln Gly Gly
        275             280             285

Phe Gly Asn Ser Arg Gly Gly Gly Ala Gly Leu Gly Asn Asn Gln Gly
    290             295             300

Ser Asn Met Gly Gly Gly Met Asn Phe Gly Ala Phe Ser Ile Asn Pro
305             310             315             320

Ala Met Met Ala Ala Ala Gln Ala Ala Leu Gln Ser Ser Trp Gly Met
            325             330             335

Met Gly Met Leu Ala Ser Gln Gln Asn Gln Ser Gly Pro Ser Gly Asn
            340             345             350

Asn Gln Asn Gln Gly Asn Met Gln Arg Glu Pro Asn Gln Ala Phe Gly
            355             360             365

Ser Gly Asn Asn Ser Tyr Ser Gly Ser Asn Ser Gly Ala Ala Ile Gly
            370             375             380

Trp Gly Ser Ala Ser Asn Ala Gly Ser Gly Ser Gly Phe Asn Gly Gly
385             390             395             400

Phe Gly Ser Ser Met Asp Ser Lys Ser Ser Gly Trp Gly Met
                405             410

( 2 ) INFORMATION FOR SEQ ID NO:2:

(i) SEQUENCE CHARACTERISTICS:
    (A) LENGTH: 1272 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| ATGTCTGAAT | ATATTCGGGT | AACCGAAGAT | GAGAACGATG | AGCCCATTGA | AATACCATCG | 60 |
| GAAGACGATG | GGACGGTGCT | GCTCTCCACG | GTTACAGCCC | AGTTTCCAGG | GGCGTGTGGG | 120 |
| CTTCGCTACA | GGAATCCAGT | GTCTCAGTGT | ATGAGAGGTG | TCCGGCTGGT | AGAAGGAATT | 180 |
| CTGCATGCCC | CAGATGCTGG | CTGGGGAAAT | CTGGTGTATG | TTGTCAACTA | TCCAAAAGAT | 240 |
| AACAAAAGAA | AAATGGATGA | GACAGATGCT | TCATCAGCAG | TGAAAGTGAA | AAGAGCAGTC | 300 |
| CAGAAAACAT | CCGATTTAAT | AGTGTTGGGT | CTCCCATGGA | AAACAACCGA | ACAGGACCTG | 360 |
| AAAGAGTATT | TTAGTACCTT | TGGAGAAGTT | CTTATGGTGC | AGGTCAAGAA | AGATCTTAAG | 420 |
| ACTGGTCATT | CAAAGGGGTT | TGGCTTTGTT | CGTTTTACGG | AATATGAAAC | ACAAGTGAAA | 480 |
| GTAATGTCAC | AGCGACATAT | GATAGATGGA | CGATGGTGTG | ACTGCAAACT | TCCTAATTCT | 540 |
| AAGCAAAGCC | AAGATGAGCC | TTTGAGAAGC | AGAAAAGTGT | TTGTGGGGCG | CTGTACAGAG | 600 |
| GACATGACTG | AGGATGAGCT | GCGGGAGTTC | TTCTCTCAGT | ACGGGGATGT | GATGGATGTC | 660 |
| TTCATCCCCA | AGCCATTCAG | GGCCTTTGCC | TTTGTTACAT | TTGCAGATGA | TCAGATTGCG | 720 |
| CAGTCTCTTT | GTGGAGAGGA | CTTGATCATT | AAAGGAATCA | GCGTTCATAT | ATCCAATGCC | 780 |
| GAACCTAAGC | ACAATAGCAA | TAGACAGTTA | GAAAGAAGTG | GAAGATTTGG | TGGTAATCCA | 840 |
| GGTGGCTTTG | GGAATCAGGG | TGGATTTGGT | AATAGCAGAG | GGGTGGAGC | TGGTTTGGGA | 900 |
| AACAATCAAG | GTAGTAATAT | GGGTGGTGGG | ATGAACTTTG | GTGCGTTCAG | CATTAATCCA | 960 |
| GCCATGATGG | CTGCCGCCCA | GGCAGCACTA | CAGAGCAGTT | GGGGTATGAT | GGGCATGTTA | 1020 |
| GCCAGCCAGC | AGAACCAGTC | AGGCCCATCG | GGTAATAACC | AAAACCAAGG | CAACATGCAG | 1080 |
| AGGGAGCCAA | ACCAGGCCTT | CGGTTCTGGA | AATAACTCTT | ATAGTGGCTC | TAATTCTGGT | 1140 |
| GCAGCAATTG | GTTGGGGATC | AGCATCCAAT | GCAGGGTCGG | GCAGTGGTTT | TAATGGAGGC | 1200 |
| TTTGGCTCAA | GCATGGATTC | TAAGTCTTCT | GGCTGGGGAA | TGTAGACAGT | GGGGTTGTGG | 1260 |
| TTGGTTGGTA | TA | | | | | 1272 |

(2) INFORMATION FOR SEQ ID NO:3:

(i) SEQUENCE CHARACTERISTICS:
    (A) LENGTH: 46 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| CTGCTTTTTG | CCTGTACTGG | GTCTCTCTGG | TTAGACCAGA | TCTGAG | 46 |

(2) INFORMATION FOR SEQ ID NO:4:

(i) SEQUENCE CHARACTERISTICS:
    (A) LENGTH: 43 base pairs
    (B) TYPE: nucleic acid
    (C) STRANDEDNESS: single
    (D) TOPOLOGY: linear (ii) MOLECULE TYPE: DNA (genomic)

( x i ) SEQUENCE DESCRIPTION: SEQ ID NO:4:

CTGACGTACG TACGTACGTA CATGCGTACG TTACGGACCA TCT                43

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AATTGGAGGA AAAACTGTTT CATACAGAAG GCGT                          34

( 2 ) INFORMATION FOR SEQ ID NO:6:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CTGCTTTTTG CCTGTACTGG GTCTCTCTGG TTAGACCAGA TCTGAG             46

( 2 ) INFORMATION FOR SEQ ID NO:7:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTGACGTACG TACGTACTGG GTCTCTCTGG TTAGACCAGA TCTGAG             46

( 2 ) INFORMATION FOR SEQ ID NO:8:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CTGCTTTTTG CCTGTACGTA CATGCGTACG TTAGACCAGA TCTGAG             46

( 2 ) INFORMATION FOR SEQ ID NO:9:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTGACGTACG TACGTACGTA CATGCGTACG TTAGACCAGA TCTGAG             46

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
AAGGGGGGCT   ATAAAAGGGG   GTGGGGG                                            27
```

( 2 ) INFORMATION FOR SEQ ID NO:11:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
GCGTGCCTCA   GATGCTGCAT   ATAAGCAGCA   GCTGCTTTTT   GCCTGTACT                49
```

( 2 ) INFORMATION FOR SEQ ID NO:12:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GCGTGCCTCA   GATGCTGCAT   ATAAGCAGCT   GCTTT                                 35
```

( 2 ) INFORMATION FOR SEQ ID NO:13:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GGTTAGACCA   GATCTGAGCC   TGGGAGCTCT   CTGGCTAACT   AG                       42
```

( 2 ) INFORMATION FOR SEQ ID NO:14:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CTGCTTTTTG   CCTGTACTGG   GTCTCTCTGG   TTAGACCAGA   TCT                      43
```

( 2 ) INFORMATION FOR SEQ ID NO:15:

( i ) SEQUENCE CHARACTERISTICS:
        ( A ) LENGTH: 43 base pairs
        ( B ) TYPE: nucleic acid -continued

```
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:15:

CTGACGTACG TACGTACTGG GTCTCTCTGG TTAGACCAGA TCT                                43

( 2 ) INFORMATION FOR SEQ ID NO:16:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:16:

CTGCTTTTTG CCTGTACGTA CATGCGTACG TTAGACCAGA TCT                                43

( 2 ) INFORMATION FOR SEQ ID NO:17:

( i ) SEQUENCE CHARACTERISTICS:
            ( A ) LENGTH: 43 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:17:

CTGACGTACG TACGTACGTA CATGCGTACG TTACGGACCA TCT                                43
```